US 8,777,624 B2

(12) United States Patent
Klein

(10) Patent No.: US 8,777,624 B2
(45) Date of Patent: Jul. 15, 2014

(54) WELLNESS AND WEIGHT MANAGEMENT SYSTEM AND METHOD

(71) Applicant: Laura Klein, Fort Lauderdale, FL (US)

(72) Inventor: Laura Klein, Fort Lauderdale, FL (US)

(73) Assignee: Elencee, Inc., Fort Lauderdale, FL (US)

( * ) Notice: Subject to any disclaimer, the term of this patent is extended or adjusted under 35 U.S.C. 154(b) by 0 days.

(21) Appl. No.: 13/662,594

(22) Filed: Oct. 29, 2012

(65) Prior Publication Data

US 2014/0106312 A1    Apr. 17, 2014

Related U.S. Application Data

(60) Provisional application No. 61/713,219, filed on Oct. 12, 2012.

(51) Int. Cl.
*G09B 19/00* (2006.01)

(52) U.S. Cl.
USPC ........................................................ 434/127

(58) Field of Classification Search
USPC ........................................................ 434/127
See application file for complete search history.

(56) References Cited

U.S. PATENT DOCUMENTS

| | | | | |
|---|---|---|---|---|
| 7,044,739 | B2* | 5/2006 | Matson | 434/127 |
| 7,297,109 | B2* | 11/2007 | Brown | 600/300 |
| 7,974,881 | B2* | 7/2011 | Culver et al. | 705/15 |
| 2009/0265289 | A1* | 10/2009 | Peplinski et al. | 706/11 |
| 2009/0298021 | A1* | 12/2009 | Black et al. | 434/127 |
| 2010/0055653 | A1* | 3/2010 | Miller-Kovach et al. | 426/232 |
| 2012/0077154 | A1* | 3/2012 | Highet et al. | 434/127 |
| 2012/0295256 | A1* | 11/2012 | Castellon et al. | 435/6.11 |
| 2012/0308970 | A1* | 12/2012 | Gillespie et al. | 434/236 |

* cited by examiner

Primary Examiner — Robert J Utama
Assistant Examiner — Sadaruz Zaman
(74) Attorney, Agent, or Firm — The Concept Law Group, P.A.; Scott D. Smiley; Yongae Jun

(57) ABSTRACT

A wellness and weight management system, method, program and software application configured to provide feedback for healthy and unhealthy lifestyle decisions that accommodates a wide variety of wellness goals, behaviors, dietary preferences, activity preferences, exercise preferences and body weight objectives.

20 Claims, 27 Drawing Sheets

WELLNESS AND WEIGHT MANAGEMENT SYSTEM AND METHOD

CROSS-REFERENCE TO RELATED APPLICATION

This application claims priority to U.S. Provisional Patent Application No. 61/713,219, filed Oct. 12, 2012, the entirety of which is incorporated by reference.

FIELD OF THE INVENTION

The present invention relates generally to a wellness and weight management system, method and software application, and more particularly relates to a wellness and weight management system, method, program, and software application configured to provide feedback for healthy and unhealthy lifestyle decisions.

BACKGROUND OF THE INVENTION

Weight loss systems commonly advance the notion that simply limiting a person's food consumption in relation to their energy expenditure will result in weight loss. Typically, a person's diet is recognized as vital to a person's healthy wellbeing. It is further recognized that sleep, stress levels, smoking and activity levels, to name a few, factor into a person's wellness and resulting weight loss. Yet despite the importance of behavioral activity to weight loss programs, the prior weight loss programs do not incorporate overall wellness factors for managing weight control and wellness. Instead, common weight loss programs involve counting a person's caloric intake and advise simply ingesting a calorie value less than the total number of calories burned by that person in a typical day. A person burns energy, measured in calories, every day in order to stay alive. For example, a number of calories are burned during sleep determined by, for example, a person's height, age and weight. However, research is beginning to show that not all calories are created equally. The composition of the food, not just the caloric value, affects weight loss and overall health. For instance, table sugar is considered a simple carbohydrate with no additional nutritional value except providing energy or calories. When sugar is eaten, insulin levels increase in the body, which in turn allows cells to receive more glucose than may otherwise be needed. Glucose that enters the cells, but is not utilized or burned, is then stored as fat. Two cups of spinach, on the other hand, which has the same caloric value as one teaspoon of table sugar, has a different nutrient composition, more positively affecting a person's overall wellness and resulting weight loss differently. Spinach has very little simple carbohydrates and does not cause an insulin spike and resulting fat storage like that of table sugar.

One well-known diet is based on points, wherein point values are assigned to each particular piece of food. The diet requires that the dieter, when the points are added together, not exceed a certain point value. The points relate to a formula which considers only the calories, fat and fiber, not the nutritional value or wellness impact, of the food. Additionally, only positive point values are assigned. In other words, the score only moves up, but does not move down, and thus, it is hard to determine individual setbacks. In addition, this particular diet is cumbersome and difficult to follow as it requires that the person determine the point value for each individual food item. These types of diets may seem insurmountable because the dieter may want to lose in excess of 50 lbs. Additionally, dieters become discouraged by limited food choices and it is hard to monitor human behaviors. In addition, this type of diet does not factor in behaviors and activities, other than physical activity. Furthermore, this type of diet requires the use of a traditional food log.

Traditional food logs have proven to be an ineffective strategy for weight loss when viewed in light of the ever enlarging waistlines of the human population. In fact, there are a number of shortcomings with tradition food logs. For example, it is unpractical for people to precisely log every food item that is consumed in a typical day. It becomes particularly burdensome when eating at restaurants, because the portion size and ingredient list is not always readily available. Furthermore, food logging is tedious and time-consuming. For instance, in a particular point-based diet, the dieter must weigh and measure each and every food item for a precise calculation relating to every calorie consumed. Additionally, it is not immediately clear the portion of, for example, a 6 oz. serving of fish. Traditional food logs focus on calories and not the quality of foods consumed or the dietary recommendations of the individual dieter.

Behaviors people perform each day may either negatively or positively impact overall wellness, including the risk of diseases, cancers, health conditions, life expectancies, and body weight. Studies have shown that 40% of all deaths in the United States are linked to four behaviors: poor nutrition, low levels of physical activity, smoking and exposure to smoke and alcohol consumption. It is widely recognized that eating a balanced diet, maintaining a healthy weight, exercising and getting enough sleep are all healthy behaviors which positively impact the physiological and psychological well-being of human beings. Likewise, eating too much fast food, consuming saturated fat and/or trans-fats, being sedentary and not getting enough sleep are all un-healthy behaviors that negatively impact the physiological and psychological well-being of human beings. Wellness and weight management are multi-dimensional health concerns that these types of regimes do not fully address.

Therefore, in spite of existing dietary plans, a need exists to overcome the problems with the prior art as discussed above. Namely, a need exists for a system and method for wellness and weight control that provides feedback about impactful wellness behaviors as well as providing a convenient and simplistic ability to track daily health and wellness factors.

SUMMARY OF THE INVENTION

The invention provides a wellness and weight management system and method that overcomes the hereinafore-mentioned disadvantages of the heretofore-known devices and methods of this general type. It is an object of the present invention to provide a wellness and weight management system, process, and application software that accommodates a wide variety of wellness goals, behaviors, dietary preferences, activity preferences, exercise preferences and body weight objectives.

It is an object of the present invention to provide a process for improving human wellness, the process including the step of receiving at least one input based on a user-consumed food, a user activity, a user behavior, and more. A value is assigned to each input, the value being a positive, negative, or neutral value. Next, a total credit value is calculated based on the summed values assigned to each input. Further, a total credit value, in relation to a target credit goal, is displayed to the user. The total credit value allows the user to evaluate their daily behaviors with the goal of regular improvement until a desired wellness outcome is achieved.

It is yet another object of the present invention to provide a process for tracking health and wellness of a person, the process including the step of receiving a plurality of inputs based on a combination of at least one user consumed food, at least one user activity, and/or at least one user behavior. The process further includes relating at least one positive value to one of the plurality of inputs, relating at least one negative value to one of the plurality of inputs, calculating a total credit value based on the positive and negative values, the total credit value being reduced in relation to the at least one negative value or increased in relation to the at least one positive value, and causing the total credit value in relation to a target credit goal to display to the user.

Although the invention is illustrated and described herein as embodied in a wellness and weight management system and method, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
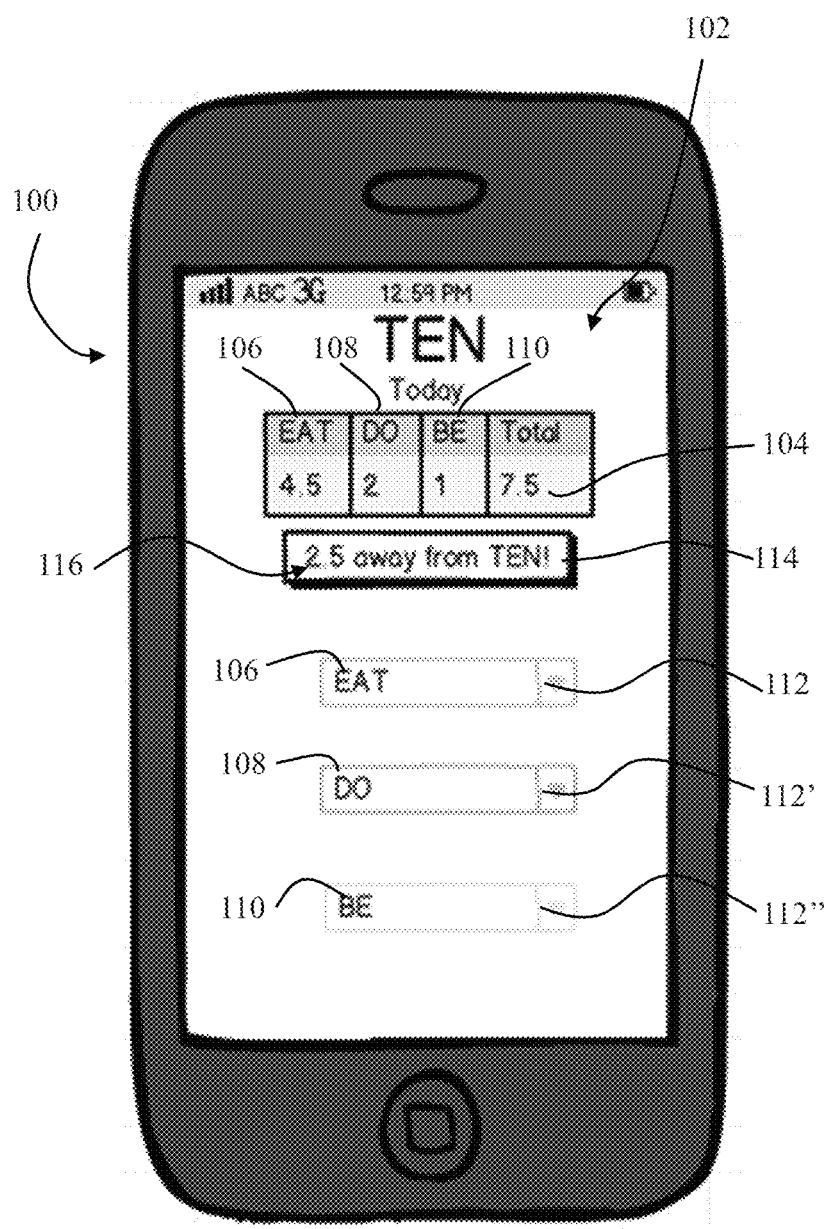
FIG. 1 is an elevational view of the front face of a mobile device displaying an exemplary weight and health management application, in accordance with the principles of the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient wellness and weight management system, method, and software application that calculates and provides feedback to a user for achieving particular wellness and weight management goals Accordingly, it is an object of the present invention to provide a program that encourages healthy behaviors and actions through feedback of impact of the both healthy and unhealthy (1) foods, (2) activities, and (3) behaviors. The invention provides credits having either positive, negative, or neutral values based on the wellness impact of the person's behaviors. The credits are provided for foods (including drinks), activities, and/or certain behaviors. The dietary log includes a food log that reinforces a healthy lifestyle through a focus on impactful food groups and easy serving sizes. It is particularly useful to use credits, having positive and negative values, to provide instant feedback as to the positive or negative effect of the food, activity and behavior choices that the user is making. Additionally, there may be a timeframe for which to reach a particular credit total, such as over the course of a day, week, month, or year. However, negative choices may reduce the particular credit total. Too many negative choices may result in that person missing the credit total goal.

It is a further object of the present invention to provide a process for wellness and body weight management in a human being. The process includes grouping impactful behaviors, impactful activities, and impactful foods ("Impact Groups" or "IG") based on similarities and wellness impacts for which that behavior, activity and/or food has on the risk of disease, cancer, health conditions, body weight, and others.

FIG. 1 provides an elevational view of the front face of a computing device 100. In this case, a mobile phone is shown, but the invention is in no way limited to any particular device and can include laptop computers, desktop computers, tablets, and other similar computing devices. The computing device displays a novel weight and health management application 102 that operates in accordance with the principles of the present invention. The wellness application 102 may be a software program installed on the computing device 100. Alternatively, the wellness application 102 may be a web-based program utilized through an internet browser on the computing device 100. The wellness application 102 provides user feedback relating to overall wellness. The feedback may include, for example, a negative, neutral, or positive overall wellness value.

Impact Factor Values ("IF Values") are calculated in accordance with certain embodiments of the present invention. Any particular IF Value may be a real number having a positive, negative, and/or no value including whole numbers, integers and rational numbers. In an embodiment, the IF Value=R+P wherein R is defined as the relationship to overall wellness impact and wherein P is defined as the likelihood of the average person performing the behavior. R may be any positive, negative or neutral value and may further indicate a strongly positively related, strongly negatively related, weakly positively related, weakly negatively related, neutral relationship to overall wellness. P may be any positive, negative or neutral value. The IF Values should encourage or discourage a person performing the behavior in order to accumulate an Impact Score towards attaining the daily goal.

As shown in FIG. 1, the IF Values can be added together to derive the total credits earned, which are graphically displayed on the computing device in field 104. The total credits earned 104 define an "Impact Score" wherein the Impact Score relates to the impact that food, activities, and behaviors will have on the health and wellness of the user. The IF Values may vary depending on previous IF Values earned. For example, boundaries exist where additional behaviors in the same IG have incrementally diminishing returns. Alternatively, boundaries exist where additional behaviors in the same IG have incrementally expanding returns. For example, a user who eats fast food may lose zero point five (0.5) credits for a first visit to a fast food establishment in a particular time period. However, a user that eats fast food may lose one (1) credit for a second visit to the fast food establishment in that same time period, thus resulting in a total of one point five (1.5) credits to be subtracted from the total credits earned 104 during a particular tracking duration. Additionally, the total distance 116 away from the target goal 114 will increase in relation to the Impact Score. In a particular embodiment, the target goal 114 is to reach a total of ten (10) credits in a specific period of time. However, it is appreciated that any credit value may be the target goal 114. In yet another example, alcoholic drinks, such as wine and/or beer, may include a positive IF Value for providing a positive credit to the total earned credits 104 because alcoholic drinks are known to have positive health benefits when consumed in small quantities and in moderation, wherein the IF Value provides incrementally diminishing returns as quantities of alcoholic drinks increase beyond a healthy level. Thus, while a first alcoholic drink may provide a positive IF Value, the IF Value may decrease to zero (0), i.e., a neutral value, or alternatively may be a negative value, such as negative one (−1) credit acting to reduce the total earned credits, Impact Score, for at least one particular time period. Alternatively, a first alcoholic drink may provide for a neutral value of zero (0) and additional alcoholic drinks may be assessed a negative value. Additionally, certain activities may have a greater IF Value when typically performed less often. For example, a user who flosses their teeth often may receive less value for an individual flossing session than an individual who rarely flosses.

The target goal 114 may be in relation to a daily goal, weekly goal, monthly goal or yearly goal or any other specified duration. Additionally, the application 102 may display a plurality of target goals 114. The goals may relate to a variety of goals, such as a weekly, monthly and/or yearly goal. As an example, a first daily target goal is provided for a ten (10) credit value and a second thirty (30) day goal is provided for a three hundred (300) credit value. The credit value for any target goal may be of any value.

Particular IF Values may be associated with behaviors that relate to a specific disease state or condition, such as Type 2 Diabetes, Cardiovascular Disease, Arthritis or Allergies.

Groups may be associated with particular food groups. Food groups may be any determined grouping of individualized food items. Alternatively, groups may be arranged in relation to the United States Department of Agriculture, USDA, recognized food groups, such as Fruits, Vegetables, Protein, Grain and Dairy.

Behaviors may be defined as any type of human behavior that affects overall wellness and/or weight management or both.

A serving size may be related to conventional serving sizes determined based on weight, volume, or other known serving sizes. Alternatively, a serving size may be determined based on a generic serving size. For example, the serving size may relate to the size of the user's fist, as the size of a user's fist has been found to generally correlate to a proper serving size in relation to the IF values. For example, a small female having a small fist needs a smaller serving size than a large male having a large fist in order to positively affect health and wellness. A serving size may be defined as any size serving capable of being accurately or approximately measured and/or quantified.

Impact Groups may include a particular threshold value for which IF Values have a predetermined maximum threshold. For example, an activity, such as sleep, may have a maximum IF Value capable of providing credits towards the total earned credits 104.

Referring now to FIG. 1, one embodiment of the present invention is shown. FIG. 1 shows several advantageous features of the present invention, but, as will be described below, the invention can be provided in several shapes, sizes, combinations of features and components, and varying numbers and functions of the components. FIG. 1 depicts a computing device 100 such as a smartphone, tablet, or any other computing device. The computing device 100 is capable of running a wellness application 102. The information from the wellness application 102 is configured to be displayed on the display screen 115 of the computing device 100.

Figure 27:
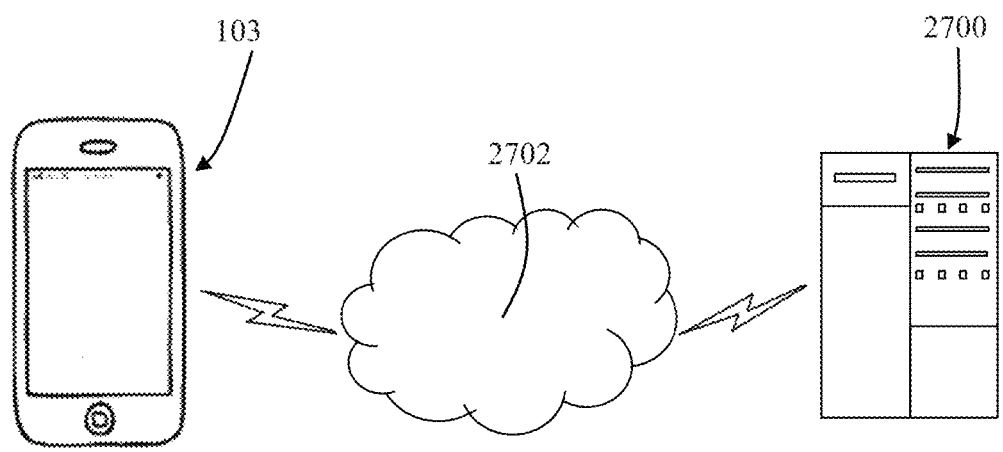
FIG. 27 is a block diagram of an exemplary weight management system that shows a smartphone device in digital communication with a server in accordance with the principles of the present invention.

In a preferred embodiment, the application 102 is run locally on computing device 100. The information may be stored locally on computing device 100 or stored in a server 2700 (shown in FIG. 27) or both. Information stored in a cloud-based server or any other type of server may be communicated across any type of network 2702, such as the internet, capable of permitting communication between the computing device 100 and the server 2700. Alternatively, the wellness application 102 may be run remotely from server 2700.

Returning to FIG. 1, the wellness application 102 is configured to display the total earned credits 104. In an embodiment, the total earned credits 104 is made up of a combination of earned credits from EAT 106, DO 108 and BE 110. EAT 106 relates to the food and drinks consumed by the user. DO 108 relates to the activities performed by the user. BE 110 relates to the behaviors experienced and/or exhibited by the user.

The wellness application provides a target goal field 114. The target goal field 114 provides a number or other indicator for which the user aims to achieve. In a particular example, the target goal may include of any combination of credits earned from EAT 106, DO 108, and BE 110, wherein the user may reach the target goal from credits from any combination of EAT 106, DO 108, and BE 110. For instance, the goal may be reached by earning credits only from food items in EAT 106. Further example, the combination of credits from EAT 106, DO 108, and BE 110 may be combined to reach the target goal. A credit total is adjusted, and displayed as adjusted on the display screen, in relation to changes to the total earned credits 104. As the total earned credits 104 moves up or down, the credits needed to achieve the target goal in field 114 moves in unison in proportionate relation. In a particular embodiment, the target goal does not fluctuate in value. For example, when the target goal is ten (10) credits, the goal will be achieved by accumulating credits that add up to the ten credits. However, negative credits may reduce the value of the total earned credits, in which case, additional credits having a positive value are required to reach the ten credit goal. For instance, if negative four (−4) credits are earned in a particular time period, then fourteen (14) credits having a positive value must be earned to reach a target goal of ten (10) credits. While the target goal in this particular example is ten (10), any positive value may be used as the target goal.

The target goal may increase in value over time as the user progresses through the wellness program. For example, the user's target goal may increase based on a variety of factors such as a fluctuation in a user's weight. Alternatively the goal may increase after the user reaches the target goal a specified number of times. In another alternative, the goal may increase after a predetermined time period.

In an embodiment, the credits needed to reach the goal may fluctuate in disproportionate relation to the total earned credits 104. For example, the user earns one negative (−1) credit that is reflected in the total earned credits 104. As a result of earning one (1) negative credit, the total credits to reach the goal will increase by two (2) credits. In yet another embodiment, earning one (1) negative credit from EAT 106, DO 108, or BE 110 increases the total specific goal of EAT 106, DO 108, or BE 108 by two (2) credits, wherein only receiving credits from that specific group of EAT 106, DO 108, or BE 108, as specified, will permit the user to reach the target goal 114. For example, if the user eats out at a fast food restaurant, having an IF Value of negative one (−1) credit in the BE category, the specific goal, such as earning three (3) BE credits as part of the ten (10) total target goal 114, will increase to four (4) BE credits, wherein four (4) BE credits are then required to reach the target goal 114.

The invention further includes at least one selection 112 configured to allow the user to select a screen to add credits for EAT 106, DO 108, and BE 110. Then at least one selection 112 is additionally configured to permit adjustment of the Impact Score.

As depicted in FIG. 1, an embodiment provides three selection menus. The first selection menu 112 allows selection of EAT 106. EAT 106 is associated with food and drink items consumed by the user of the wellness application 102. Credits are associated with the consumption of food and drink items and associated IF Values. The second selection menu 112' allows selection of DO 108. DO 108 is associated with activities of the user, wherein activities may include, inter alia, exercise, yoga, reading, sleeping, watching TV, playing video games, sitting at work, and other similar activities. The third selection menu 112" allows selection of BE 110. BE 110 is associated with behaviors of the user, wherein behaviors may include, inter alia, eating breakfast, eating fast food, eating out, smoking and/or being in a state of stress. The behaviors may further include any and all attitude or emotion experienced by the user, such as, for example, happiness, sadness, and anger.

Figure 2:
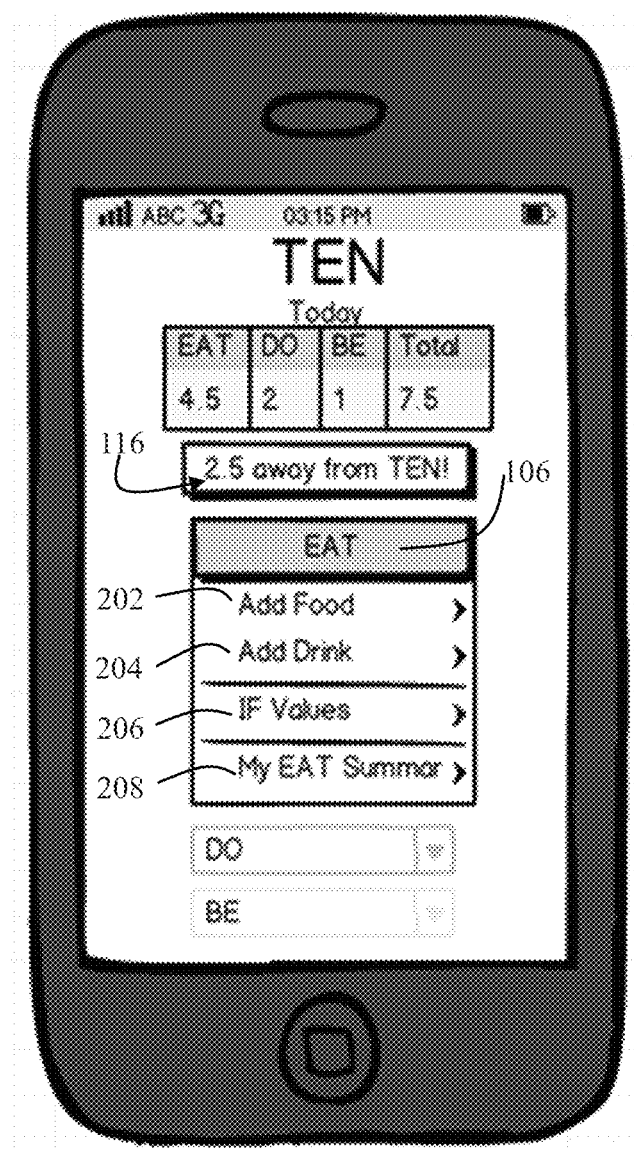
FIG. 2 is an elevational view of the front face of a mobile device featuring a graphical user interface displaying results of the application after the user selects "EAT" in accordance with the principles of the present invention.

FIG. 2 is an elevational view of the front face of the mobile device 100 featuring a graphical user interface displaying results of the application 102 after the user selects "EAT" 106 in accordance with the principles of the present invention. Selecting EAT 106 allows the user to select between adding food 202 items or adding drink 204 items in order to affect the total credits earned 104, and further to affect the total credits earned toward reaching the target goal 114. A selection 206 for determining the IF Values is available, wherein choosing selection 206 allows the user to determine the value of credits to be awarded for a particular food or drink selection. The IF Values may be between any positive or negative number, including decimals. For example, eating an apple may earn the user zero point five (0.5) EAT 106 credits. For a further example, eating a fast food hamburger may earn the user negative zero point five (−0.5) credits. A food summary selection 208 for viewing a summary of foods consumed is available for providing feedback of the wellness impact of the foods consumed by the user.

Figure 3:
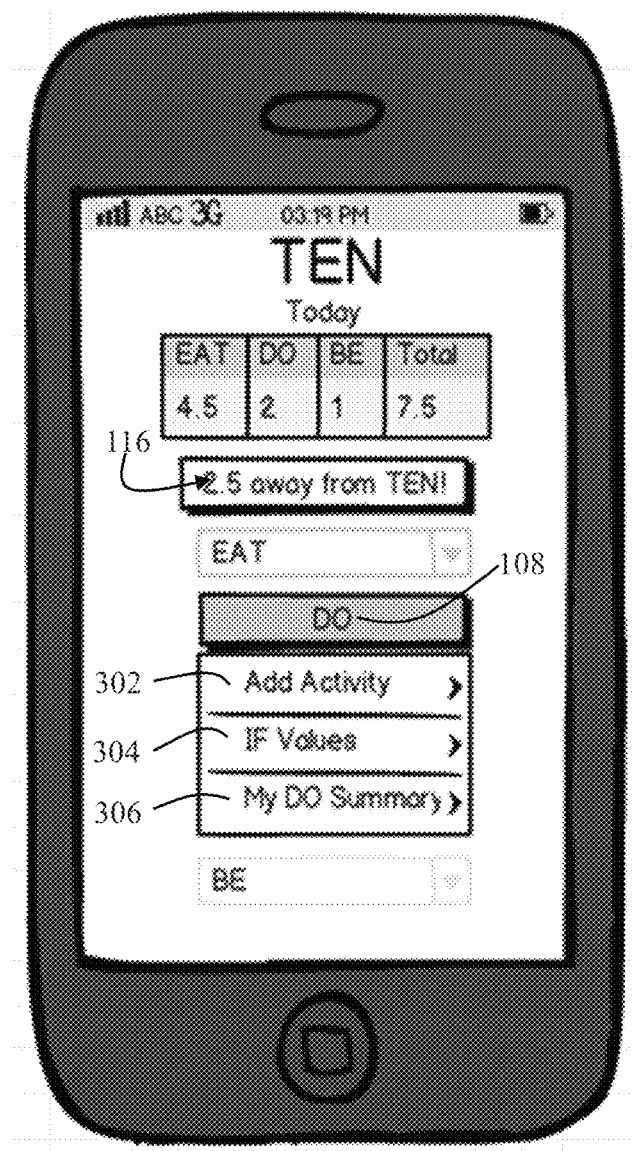
FIG. 3 is an elevational view of the front face of a mobile device featuring a graphical user interface displaying results of the application after the user selects "DO" in accordance with the principles of the present invention.

FIG. 3 is an elevational view of the front face of the mobile device 100 featuring a graphical user interface displaying results of the application 102 after the user selects "DO" 108 in accordance with the principles of the present invention. The selection 112' of DO 108 allows the user to further select items, such as, add activity selection 302 for adding an activity 302, IF Value determination selection 304 of the IF Values relating to a particular selectable activity, and activity summary selection 306 for viewing a summary of DO 108. Activities include particular activity items having a particular IF Value associated with them. Selection of a particular activity affects the total credits earned 104 towards the target goal 114. The IF Value may be between any positive or negative number, including decimals. For example, exercising may earn the user one point five (1.5) credits, moving the user closer to the target goal 114. For another example, playing video games for a particular time period may earn the user negative two point five (−2.5) credits, moving the user further away from the target goal 114. The wellness application 102 may display, in any manner, the distance 116 from the target goal 114. For example, FIGS. 1-4 depict a box displaying a target goal 114 of ten (10) and further depicts a distance of two point five (2.5) credit distance 116 from the target goal 114. A selection 304 (see FIG. 3) for determining the IF Values is available, wherein choosing selection 304 allows the user to look up the IF Value to be awarded for a particular DO 108 activity.

Figure 4:
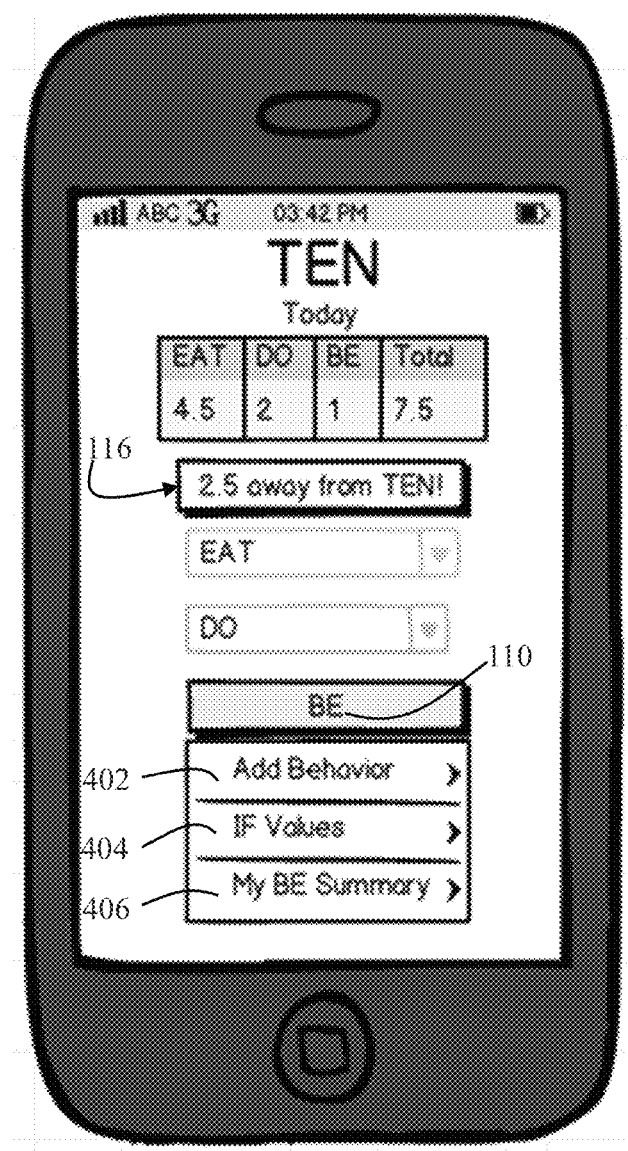
FIG. 4 is an elevational view of the front face of a mobile device featuring a graphical user interface displaying results of the application after the user selects "BE" in accordance with the principles of the present invention.

FIG. 4 is an elevational view of the front face of the mobile device 100 after the user selects "BE" 110 from the wellness application 102 in accordance with the principles of the present invention. The selection 112" (from FIG. 1) of BE 110 allows the user to further select items, such as, add behavior selection 402 for adding a behavior 110, IF Value determination selection 404 for determining the IF Values relating to a particular selectable behavior, and behavior summary selection 406 for viewing a summary of the individual behaviors having a credit value. Selection of BE 402 allows for the selection of particular behaviors, such as eating breakfast, eating fast food, smoking and taking/not taking prescribed medications, among many other possible choices. Behaviors additionally include human emotions such as stress, happiness, sadness and anxiety, each having at least a particular IF value associated to it. The IF credit value may be associated depending upon the level of the behavior. For example, if the individual is only mildly stressed, then the user may so indicate, wherein a particular value is associated thereof. User selection of a particular behavior affects the total credits earned 104 and the target goal 114. The IF Value may be between any positive or negative number, including decimals. For example, a user that indicates happiness may earn the user one point five (1.5) credits. For another example, a user that indicates stress may earn the user negative two point five (−2.5) credits. IF Value adjustment selection 404 for determining the IF Values is available, wherein choosing the IF Value selection 404 allows the user to look-up the value of credits to be awarded for a particular DO 108 activity.

Figure 5:
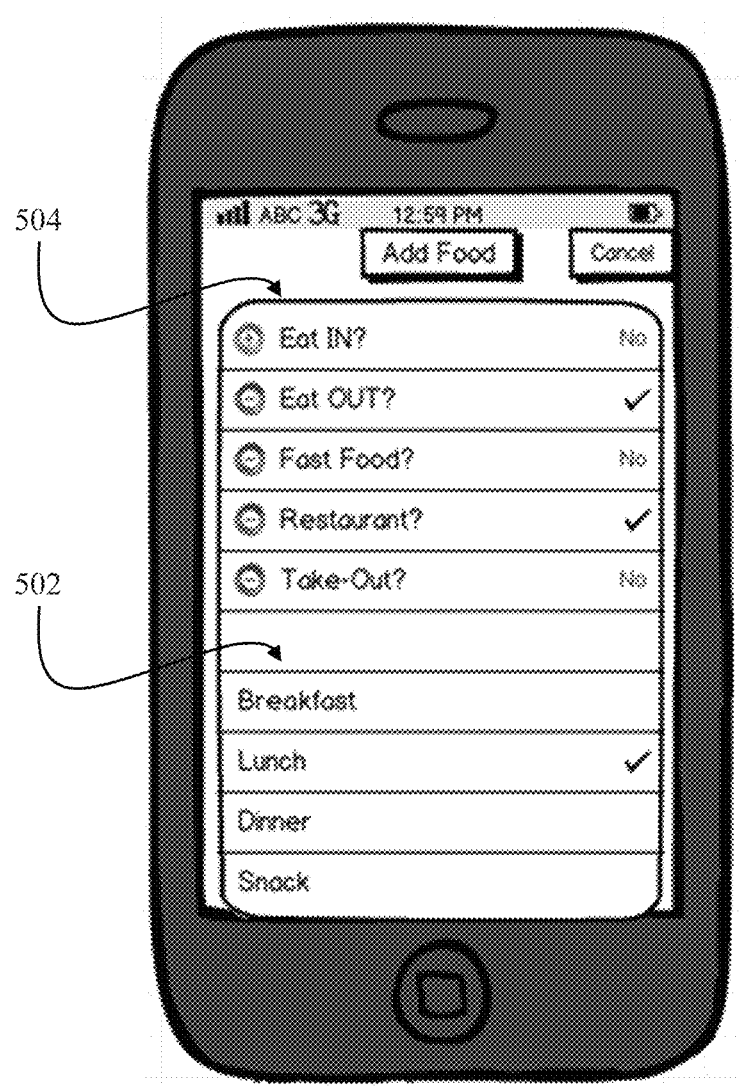
FIG. 5 is an elevational view of the front face of a mobile device featuring a graphical user interface displaying results of the application after the user selects "Add Food," from the menu shown in FIG. 2 in accordance with the principles of the present invention.

FIG. 5 is an elevational view of the front face of the mobile device 100 featuring the wellness application 102 that provides a graphical user interface displaying results of the application 102 after the user selects "Add Food," 202 from the menu shown in FIG. 2 in accordance with the principles of the present invention. The application 102 allows user selection of various options. For example, the user may make a meal selection 502 to indicate whether a particular food or drink is consumed as breakfast, lunch, dinner, or as a snack. The timing of the food or drink item may affect the credit value associated. For example, consuming an apple at 12:30 am at night may be of less credit value than consuming an apple at 8:30 am. As an additional example, consuming a first apple for breakfast may be worth a particular credit value, whereas a second apple consumed for the same breakfast may be worth another particular credit value, but possibly not the same as the first credit and can even be negative. Further, the user may make a food location selection 504 that indicates whether a particular food item is associated with eating in, such as at home or a family and friends house, or eating out. Often times, home-cooked foods have higher nutritional value than restaurant foods. Additionally, the user may indicate whether the food is fast food or restaurant food. The user may further indicate whether the food was takeout or delivery. A particular credit value may be associated with eating in, whereas a different and likely lower credit value may be associated with eating out. Studies have shown that people who eat out often tend to be more overweight than those who don't eat out as often. Similarly, a particular credit value may be associated with fast food, restaurant food, take-out or delivery.

Figure 6:
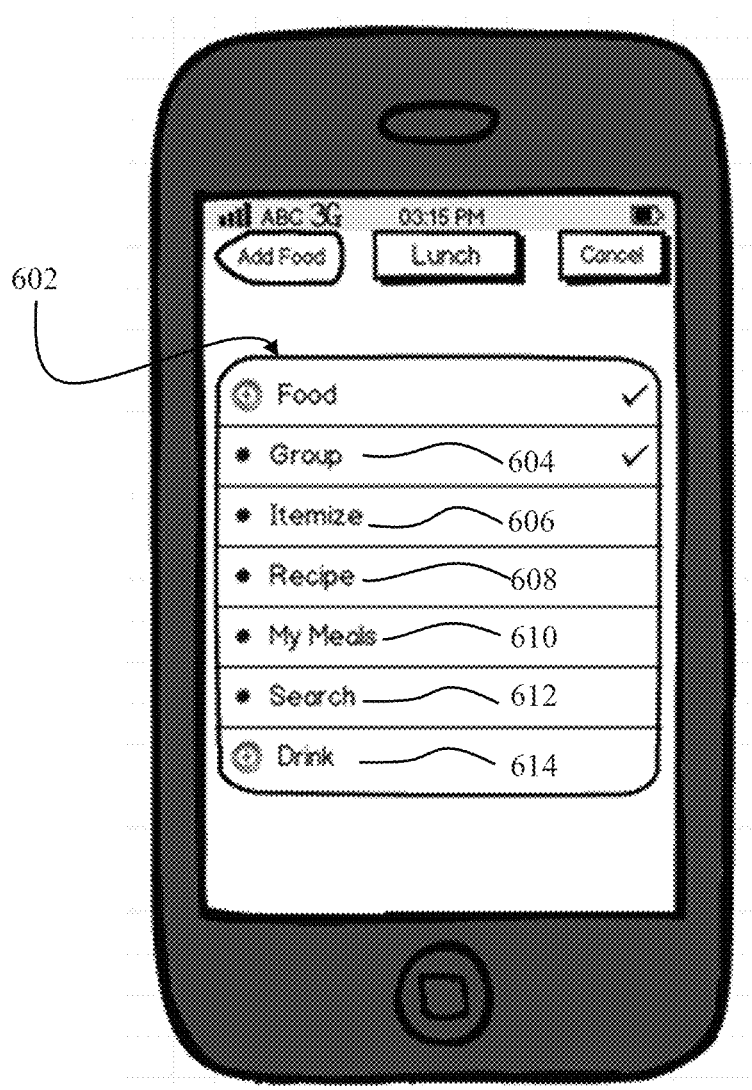
FIG. 6 is an elevational view of the front face of a mobile device featuring a graphical user interface prompting the user to select food and drink items in accordance with the principles of the present invention.
Figure 7:
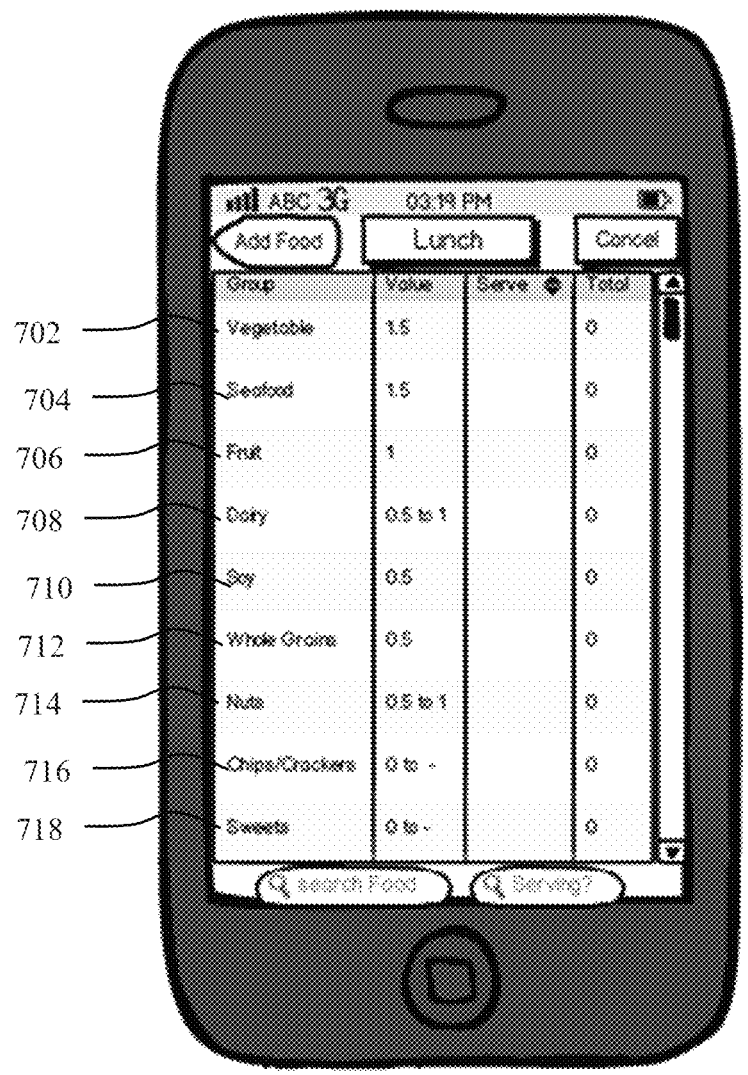
FIG. 7 is an elevational view of the front face of a mobile device featuring a graphical user interface displaying food group choices in accordance with the principles of the present invention.

FIG. 6 is an elevational view of the front face of the mobile device 100 featuring the wellness application 102 that provides a graphical user interface prompting the user to select food and drink items. FIG. 6 depicts a selection 602 for laying out food or drink items. For example, user selection of Group 604 provides a list of foods sorted by group (FIG. 7). Groups include, inter alia, Vegetables 702, Seafood 704, Fruit 706, Dairy 708, Soy 710, Whole Grains 712, Nuts 714, Chips/Crackers 716, Sweets 718 and others (FIG. 7). Selection of the itemized list input 606 will provide a further itemized list of individualized foods and drinks that are capable of selection by the user. Selection of the recipe input 608 will provide recipes formed from a combination of individual items, wherein the combination of the items have a particular IF Value represented by a particular recipe. The recipes can be maintained at a central database accessible through a network by a plurality of users. In this embodiment, a database manager is able to access each recipe and assign credit values based on aspects of the recipe that merit credit scores. In addition, recipes can have different credit scores that depend on the ingredients, i.e., organic items score higher than non-organic, low salt ingredients score higher than salted items, etc.

Selection of the My Meals input 610 will provide a list of previously selected meals. Meals may include a plurality of separate food items that are grouped together to easily select multiple food items the user commonly eats during for a meal. A search selection input 612, when selected, permits the user to search a database for a particular food or drink item. A drink selection input 614 may be selected. The drink selection input 614, when selected, will provide a selection for further selection of a drink groups, itemized list of drinks, drink recipes, and drink search.

Figure 8:
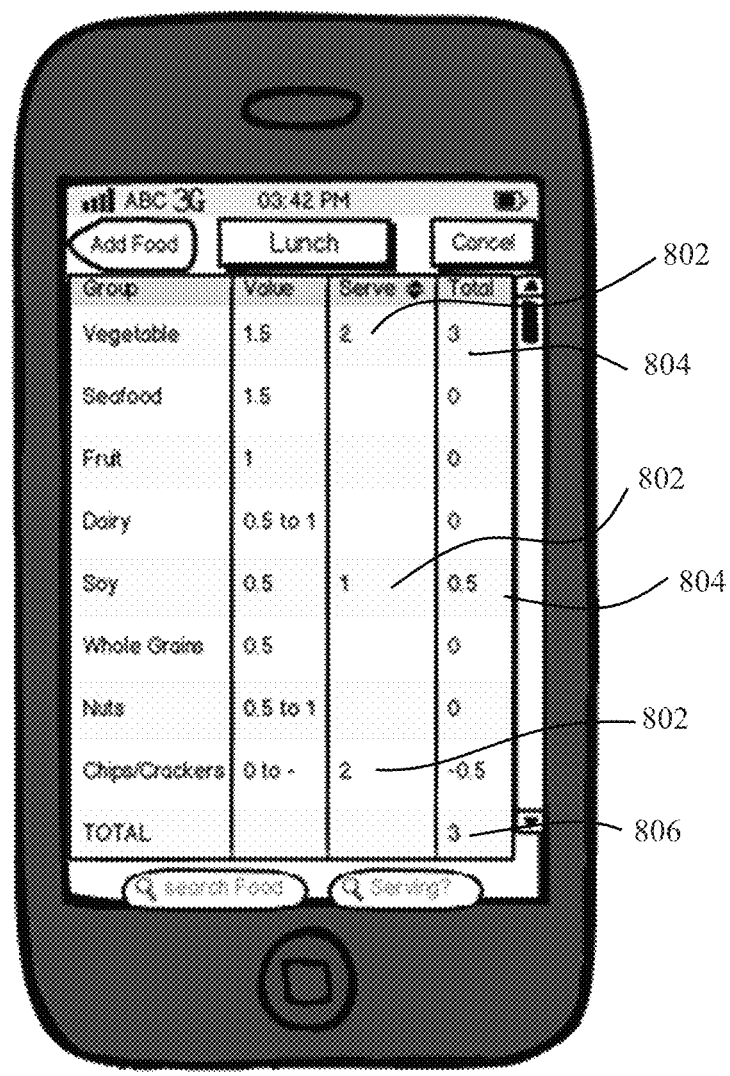
FIG. 8 is an elevational view of the front face of a mobile device featuring a graphical user interface displaying exemplary user selections in accordance with the principles of the present invention.

FIGS. 7 and 8 show the mobile device 100 displaying the wellness application 102 that permits selection of a particular food group item. The user will input the serving size 802 for each particular item that is consumed by the user. An individual group credit value 804 is calculated based upon at least the IF Value from that particular food group and the serving size. The individual group credit value 804 is displayed on the computing device 100. Each individual group credit value 804 is added together and the total group credit value 806, which includes the summation from each individual group credit value 804, is displayed on the display of the computing device 100. Furthermore, the individual group credit value is added to the total earned credits 104 (FIG. 1). Additionally, the item credit value will be subtracted from the target goal 114 (FIG. 1).

Figure 9:
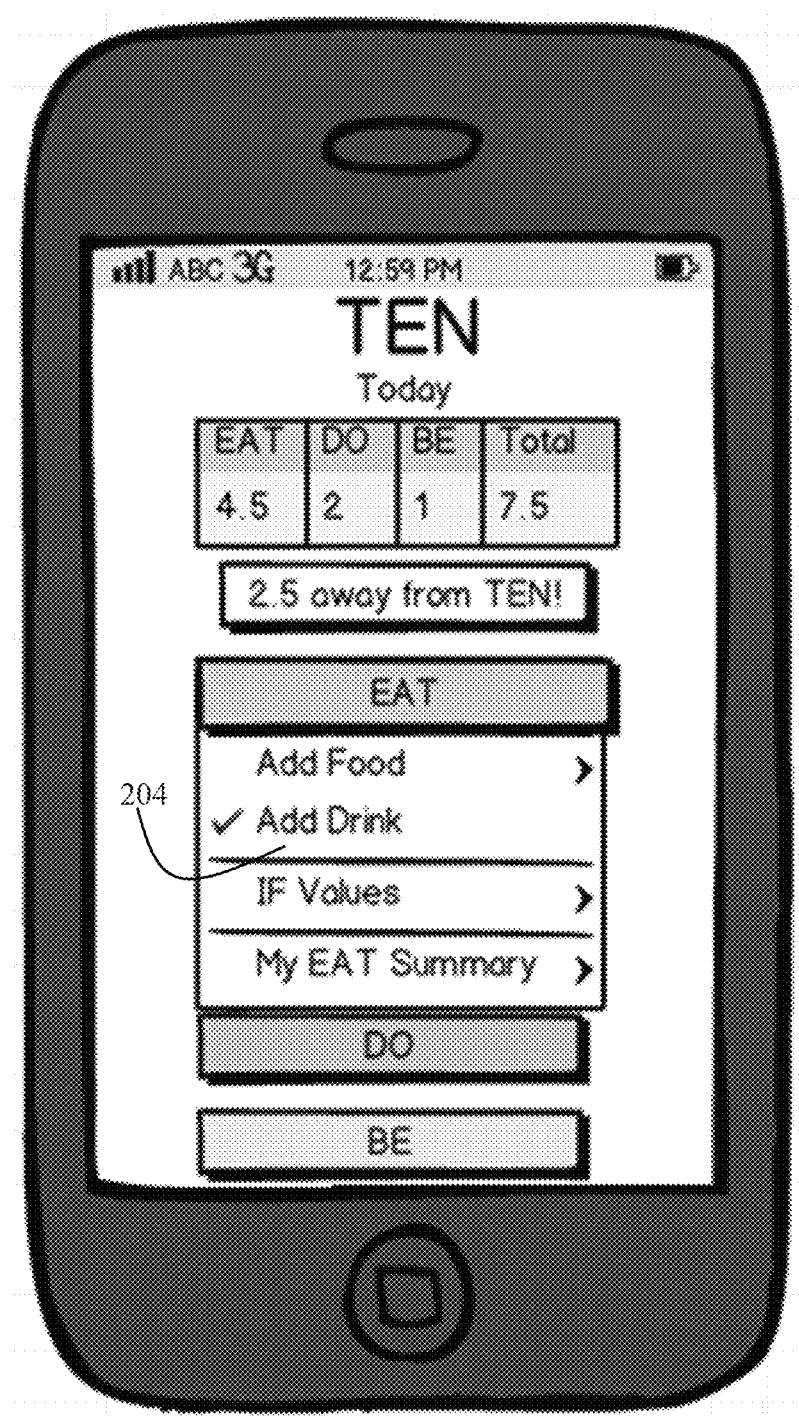
FIG. 9 is an elevational view of the front face of a mobile device featuring a graphical user interface receiving an input that a drink should be added in accordance with the principles of the present invention.
Figure 10:
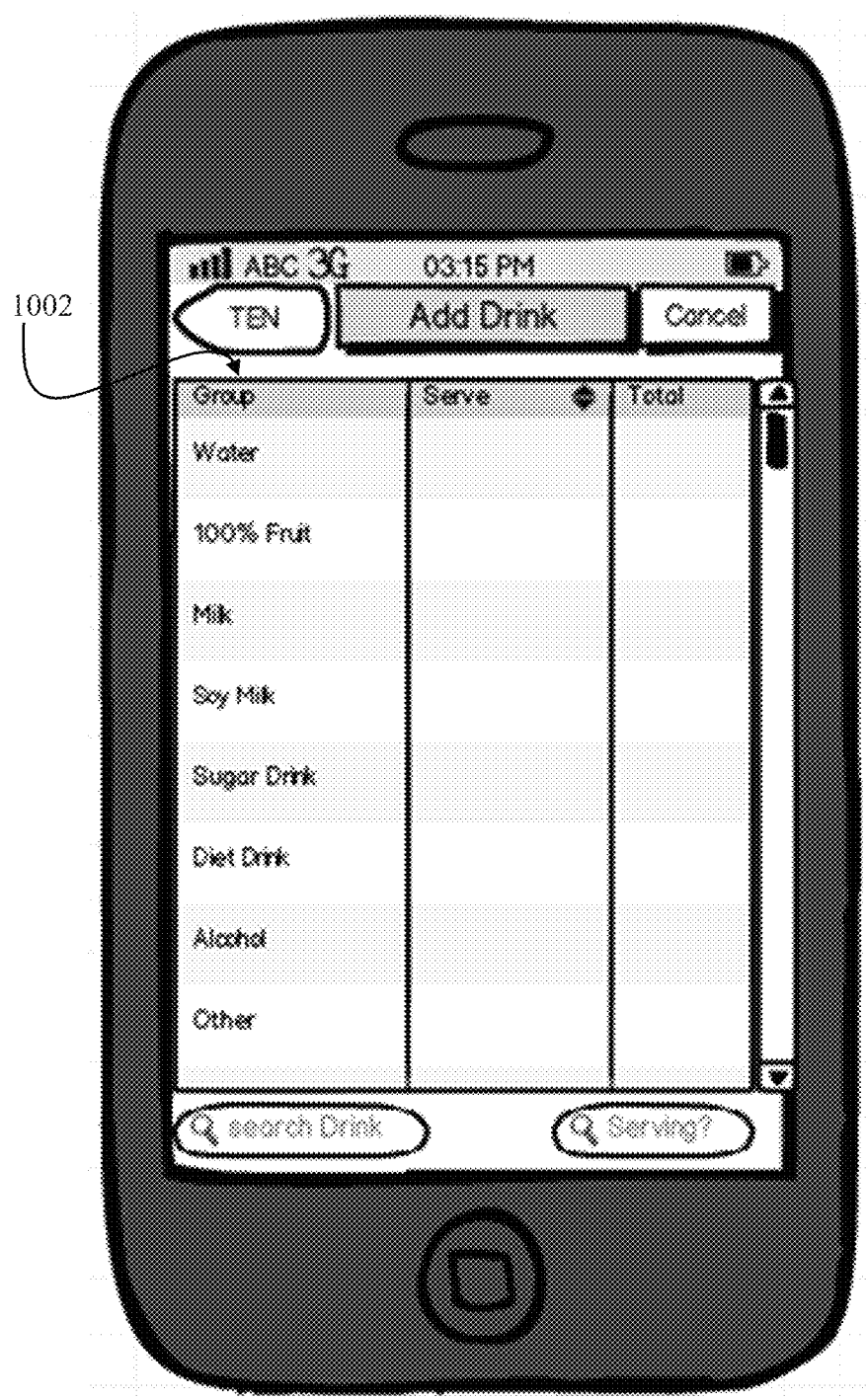
FIG. 10 is an elevational view of the front face of a mobile device featuring a graphical user interface displaying a selectable sub-menu for specifying drinks after the selection shown in FIG. 9 in accordance with the principles of the present invention.
Figure 11:
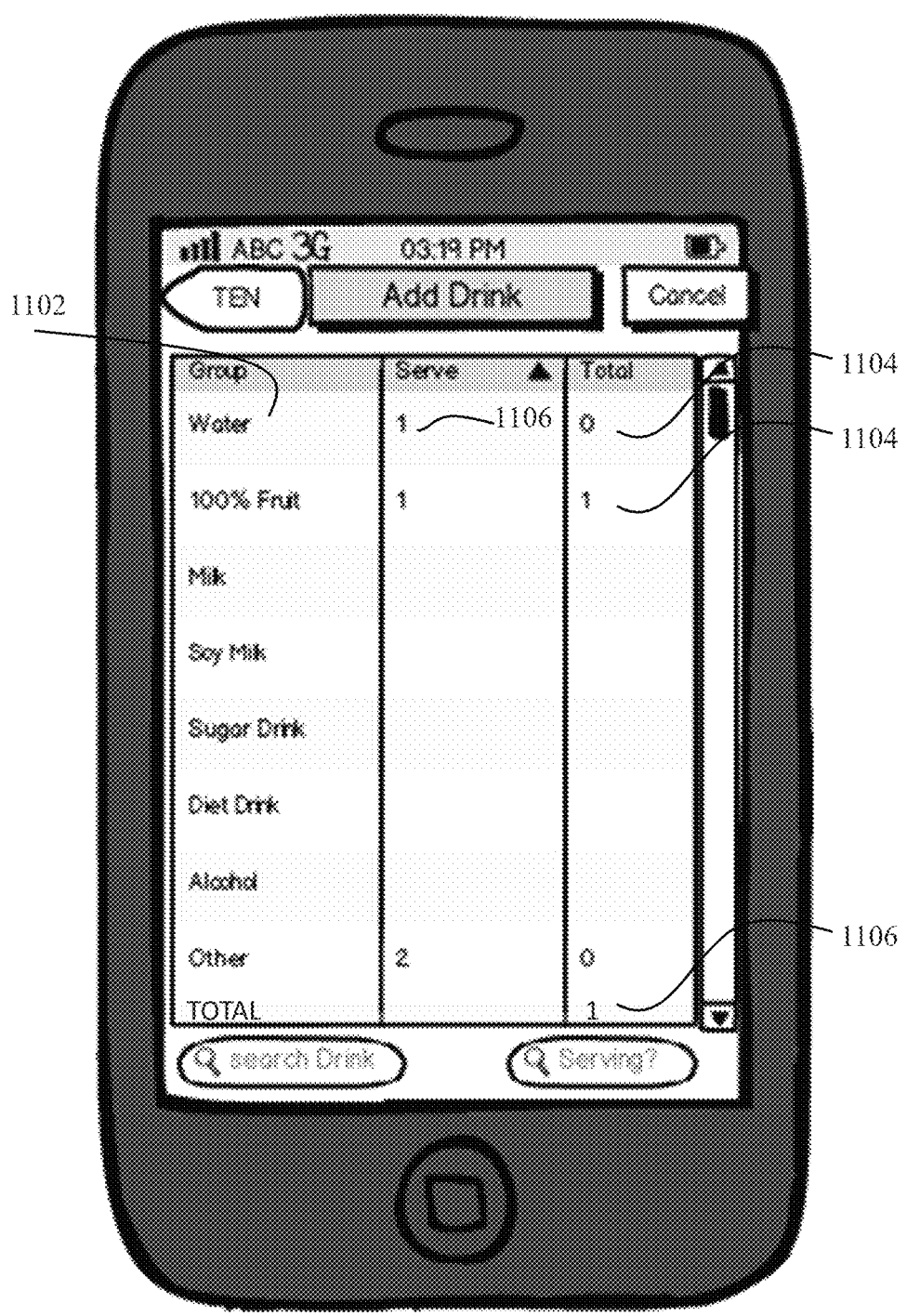
FIG. 11 is an elevational view of the front face of a mobile device featuring a graphical user interface displaying a selectable menu of drink choices in accordance with the principles of the present invention.

FIGS. 9-11 are elevational views of the front face of the mobile device 100 featuring the wellness application 102 that provides a graphical user interface displaying results of the application 102 after the user selects "Add Drink," 204 from the menu shown in FIG. 2. The user selects Add Drink 204 permitting user selection of a drink or other beverages. From the user's selection of Add Drink 204, a listing of drinks are available for selection. These drinks, from a drink selection 1002 shown in FIG. 10 may include, inter alia, water, fruit juice, milk, soy milk, sugar drink, diet drink, alcohol or other types of drinks. As one example, the user selects a drink such as water 1102 shown in FIG. 11. The user further selects the serving size 1106 also shown in FIG. 11. An individual drink credit value 1104 is calculated based upon at least the IF Value from that particular drink and serving size. The individual drink credit value 1104 is displayed the computing device 100. The total drink credit value 1106, which includes the summation from each individual drink credit value 1104 is displayed on the display of the computing device 100. Furthermore, the individual drink credit value is added to the total earned credits 104, such as that shown in FIG. 1. Additionally, the drink credit value will be subtracted from the target goal 114.

Figure 12:
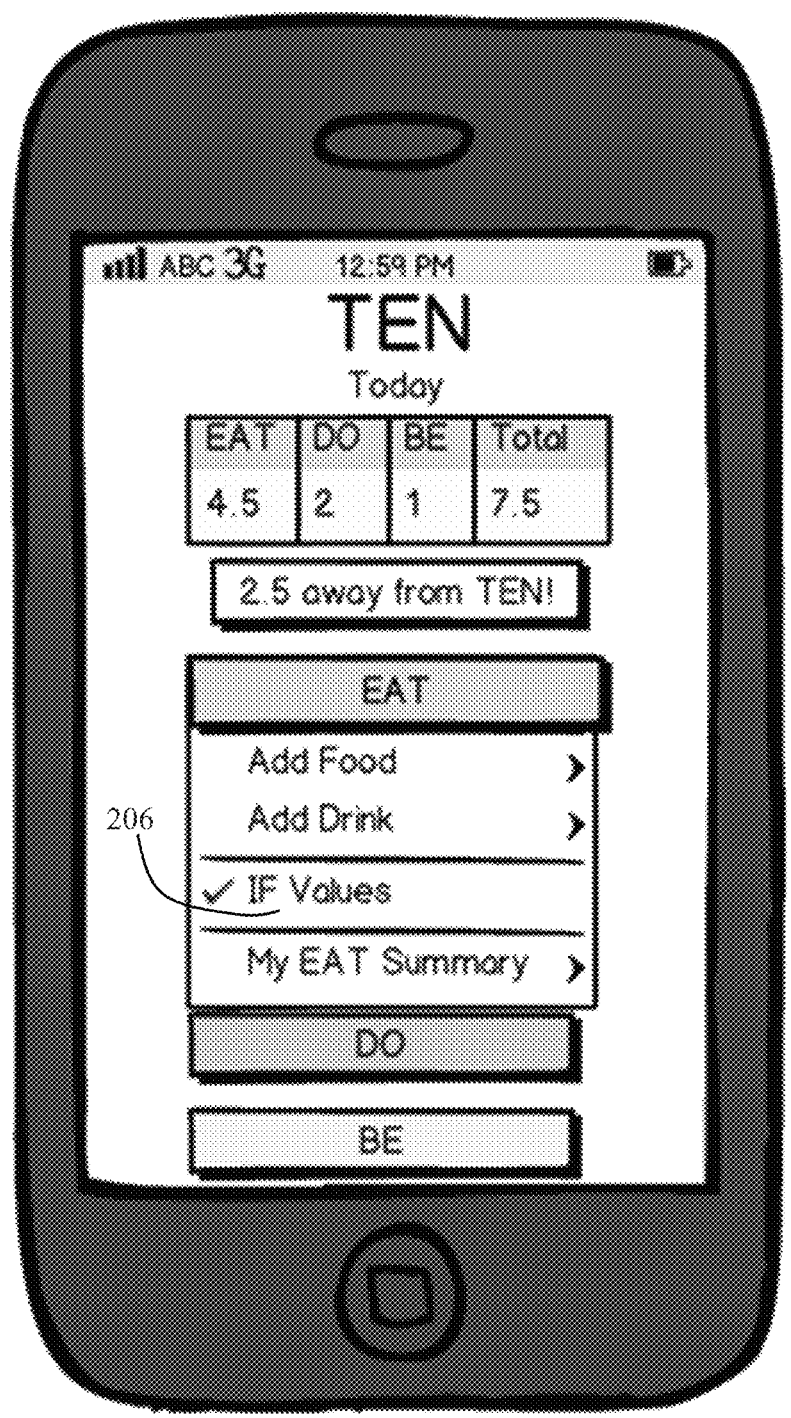
FIG. 12 is an elevational view of the front face of a mobile device featuring a graphical user interface displaying a selectable menu featuring IF Values in accordance with the principles of the present invention.
Figure 13:
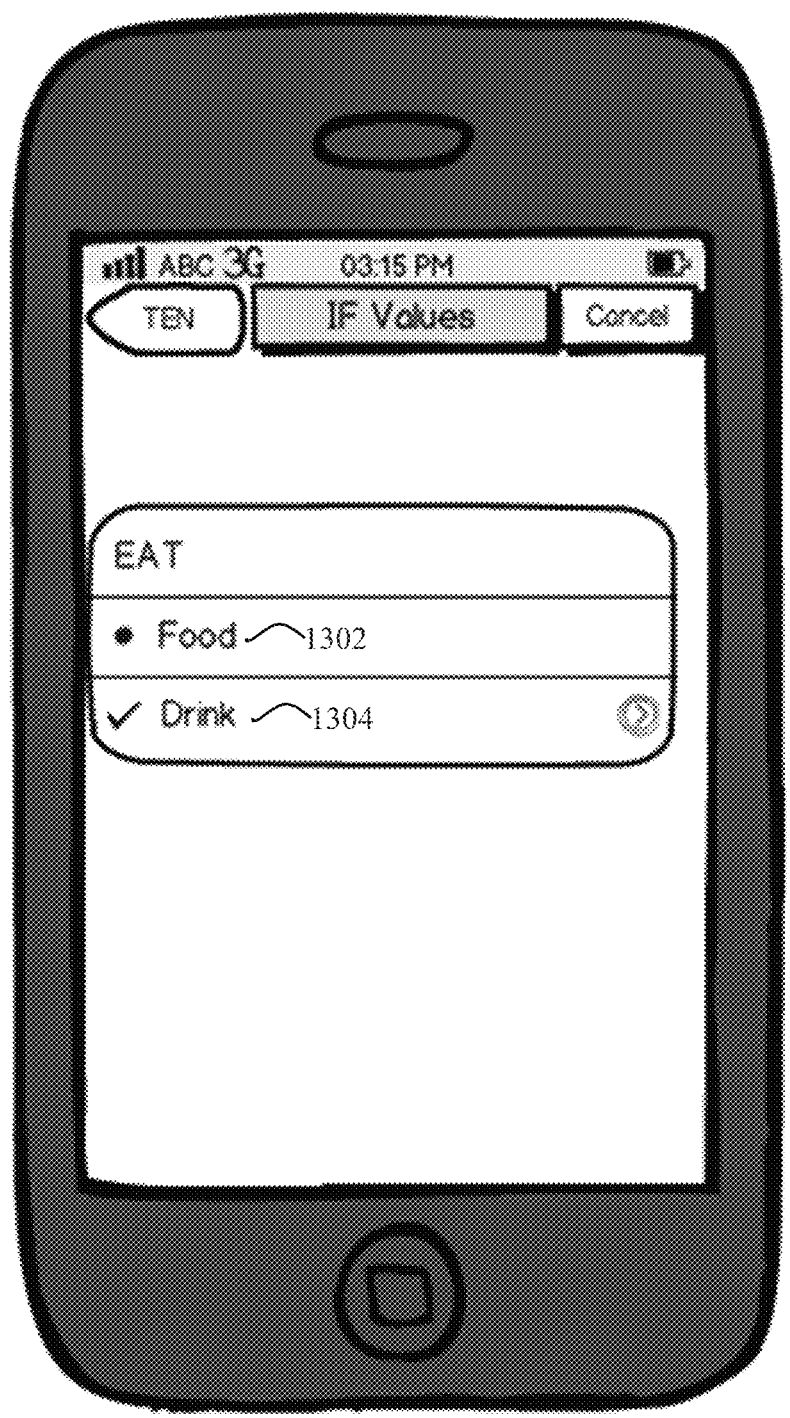
FIG. 13 is an elevational view of the front face of a mobile device featuring a graphical user interface displaying items available for selective determination in accordance with the principles of the present invention.
Figure 14:
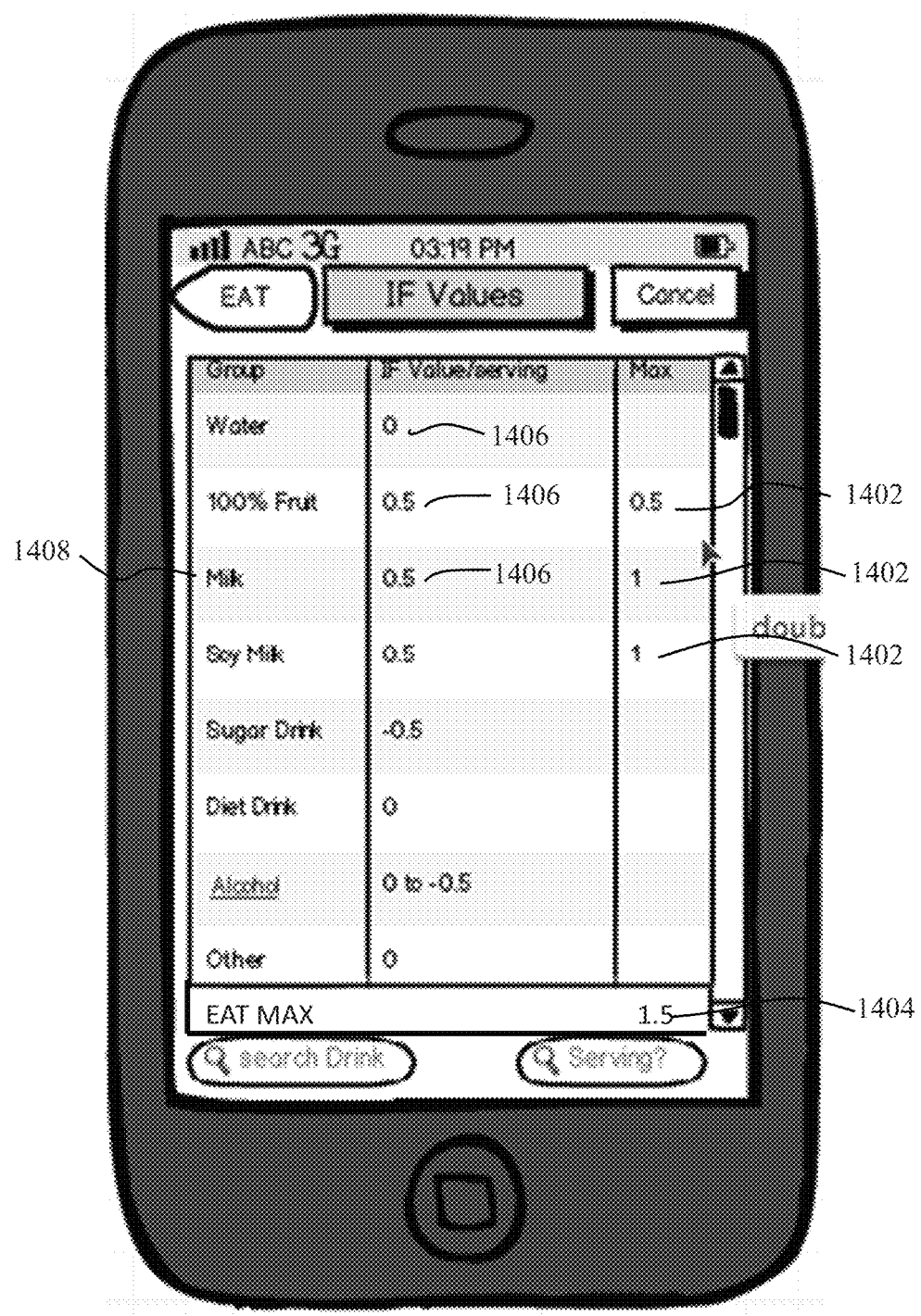
FIG. 14 is an elevational view of the front face of a mobile device featuring a graphical user interface displaying IF Values and their accumulation in accordance with the principles of the present invention.

FIGS. 12-14 are elevational views of the front face of the mobile device 100 featuring the wellness application 102 that provides a graphical user interface displaying a user selection and determination of IF Values. The user is able to activate the IF values input 206 shown in FIG. 12. The user may select whether the Food IF Values 1302 and/or Drink IF Values 1304 shown in FIG. 13. As shown in FIG. 14, the IF value 1406 is the IF Value per serving. In one embodiment, the user may select a more than one serving, but the maximum IF Value to be credited towards the total credits earned 104 is only for the one serving. Additionally, the maximum IF value may impact the credits to be subtracted from the distance away from the target goal 116 for any particular food or drink consumed by the user. For example, in FIG. 14, 1402a the maximum credit for drinking Fruit Juice is 0.5 credits. Whether the user drinks more than one serving of Fruit Juice, the user can only earn a maximum of zero point five (0.5) credits for this behavior.

In operation, for exemplary purposes, the user may select milk 1408 which has zero point five (0.5) incremental IF Value per serving. Further, milk 1408 may be set to have a maximum of one (1) credit value 1402. When the user selects one serving of milk 1408, a credit value of zero point five (0.5) credits are added to the total credits earned 104. Additionally, zero point five (0.5) credits are subtracted from the distance away from the target goal 116 when the user selects that particular food item, drink item, or group item. When the user selects 5 servings of milk, for example, only one (1) credit value is added to the total credits earned 104 because the maximum serving was set to provide 1 total credit for milk (FIG. 14). EAT 106, DO 108 and BE 110 may each be configured to have a maximum value 1404 for the IG in which the value of EAT 106, DO 108 and BE 110 may not exceed the maximum value 1404.

Figure 15:
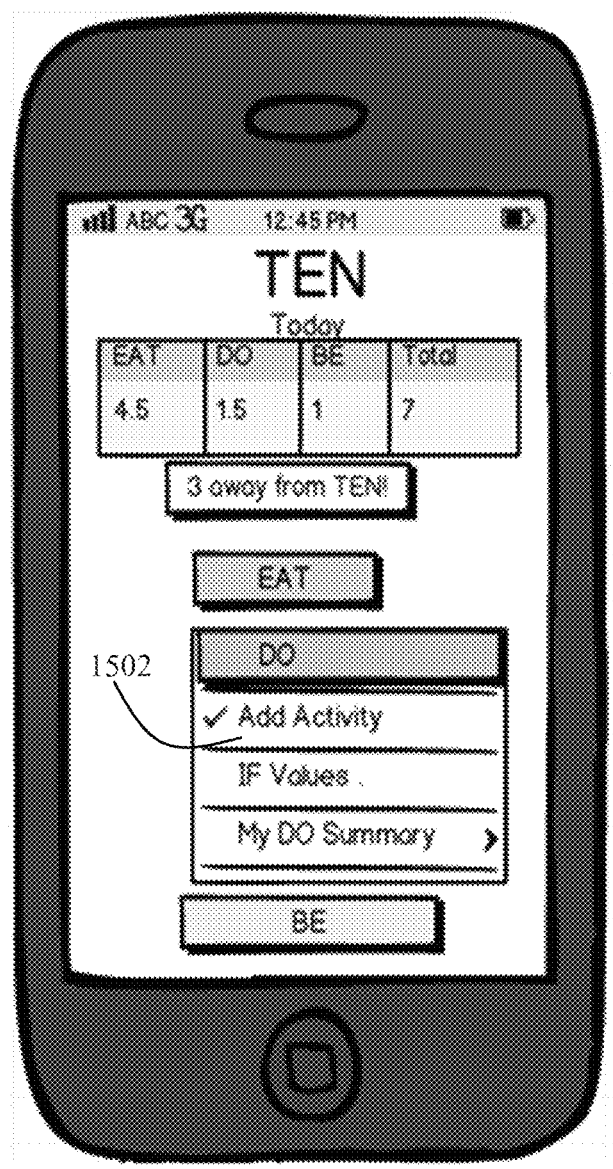
FIG. 15 is an elevational view of the front face of a mobile device featuring a graphical user interface allowing a user to add an activity in accordance with the principles of the present invention.
Figure 16:
FIG. 16 is an elevational view of the front face of a mobile device featuring a graphical user interface allowing a user selection of "Exercise" after the user selects "Add Activity" as shown in FIG. 15 in accordance with the principles of the present invention.
Figure 17:
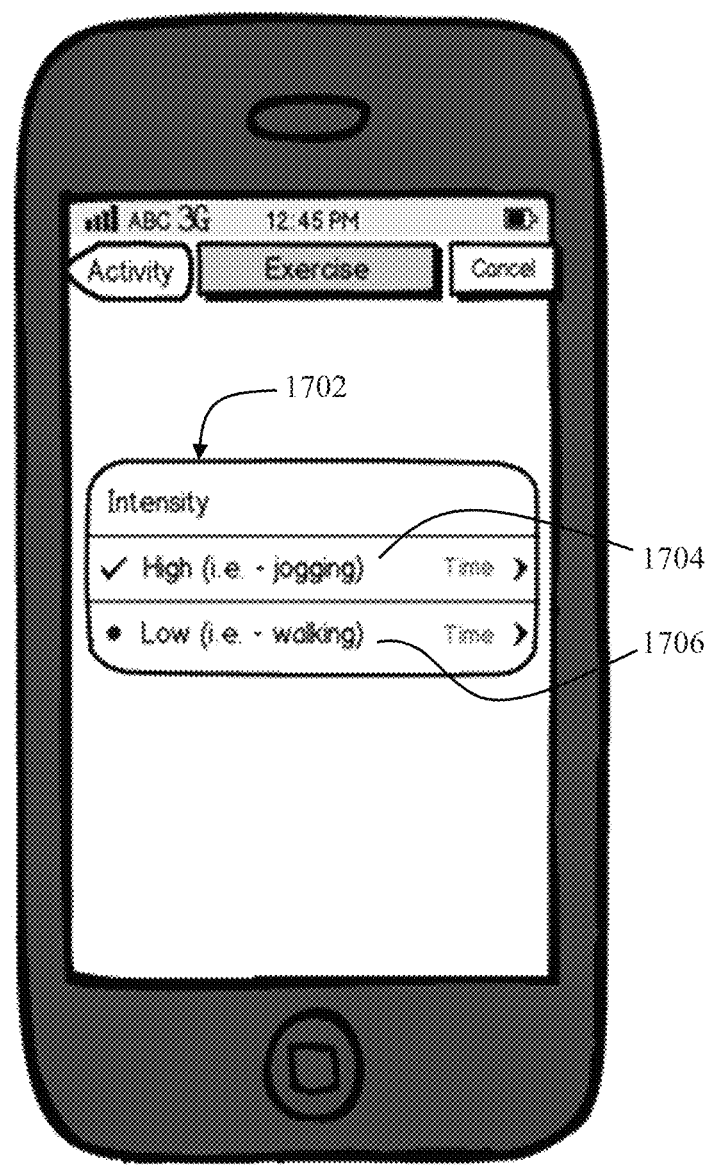
FIG. 17 is an elevational view of the front face of a mobile device featuring a graphical user interface allowing a user selection of intensity level after the user adds an activity as shown in FIG. 16 in accordance with the principles of the present invention.
Figure 18:
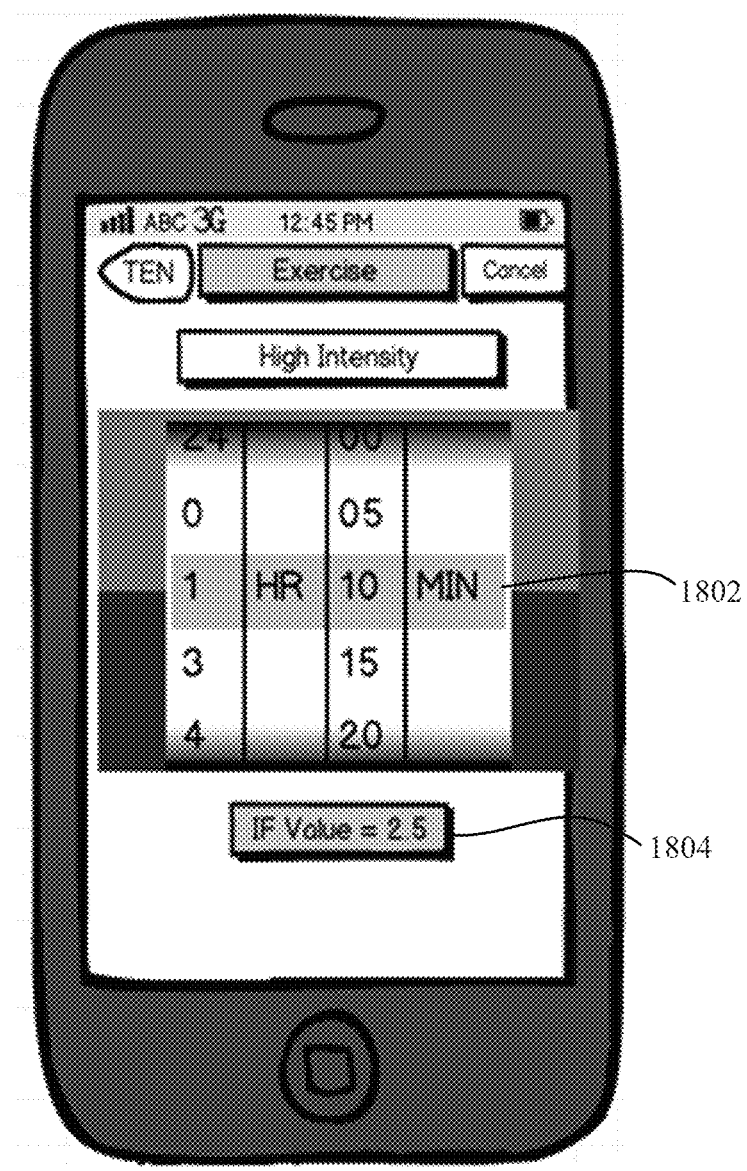
FIG. 18 is an elevational view of the front face of a mobile device featuring a graphical user interface allowing a user selection of a length of intensity after the user adds an activity as shown in FIG. 16 in accordance with the principles of the present invention.

FIGS. 15-18 are elevational views of the front face of the mobile device 100 featuring the wellness application 102 that provides a graphical user interface displaying a user selection for adding credit values associated with particular activities. The user selects "DO" 108, as shown in FIG. 3. The user then selects "Add Activity" 1502 as shown in FIG. 15. The user is then prompted to add particular activities. For example, the user may select exercise 1602, as shown in FIG. 16. Because exercise is performed at different intensity levels, selection of exercise provides for the selection of the intensity level of the exercise 1702, as shown in FIG. 17. For example, the user might select high intensity 1704 or low intensity 1706. Additionally, the user selects the duration 1802 of the activity 1602. Based on the user's selection, an IF Value is displayed to indicate the total credit value earned for the particular activity. For example, the user might select exercise 1602, at a high intensity 1704, for a total duration 1802 of one hour and ten minutes (1:10) which could provide an IF value of two point five (2.5) credits 1804 towards the total credits earned 104 (FIG. 16-18).

Figure 19:
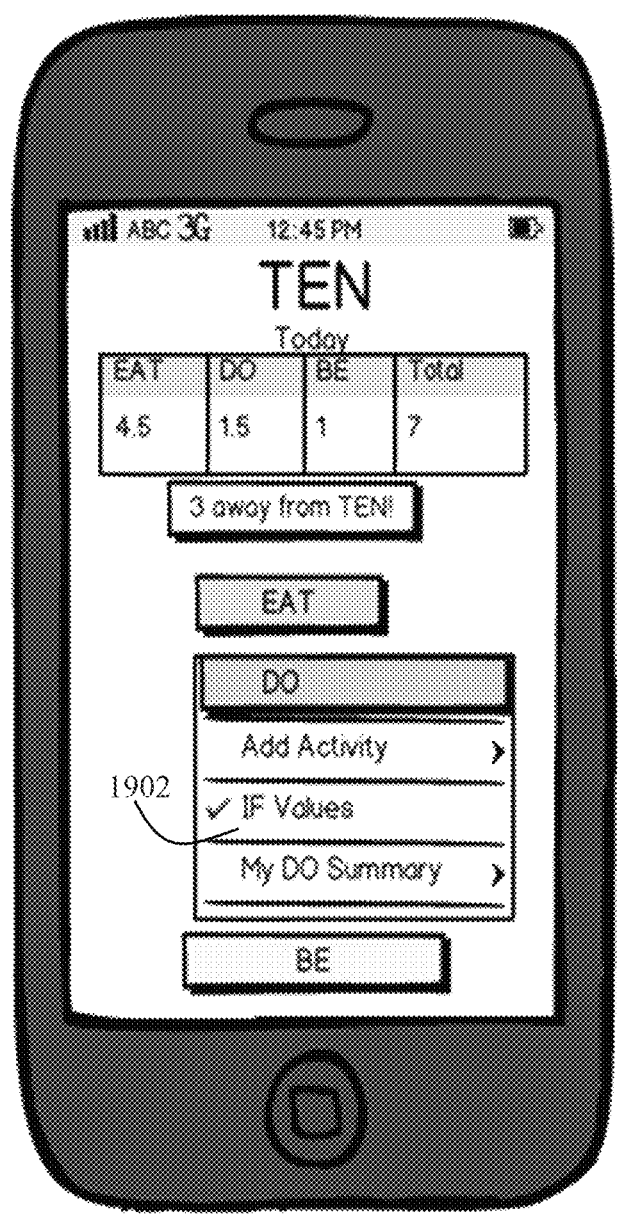
FIG. 19 is an elevational view of the front face of a mobile device featuring a graphical user interface allowing a user selection of IF Values in accordance with the principles of the present invention.
Figure 20:
FIG. 20 is an elevational view of the front face of a mobile device featuring a graphical user interface allowing a user selection of activities for IF Values assigned in accordance with the principles of the present invention.
Figure 21:
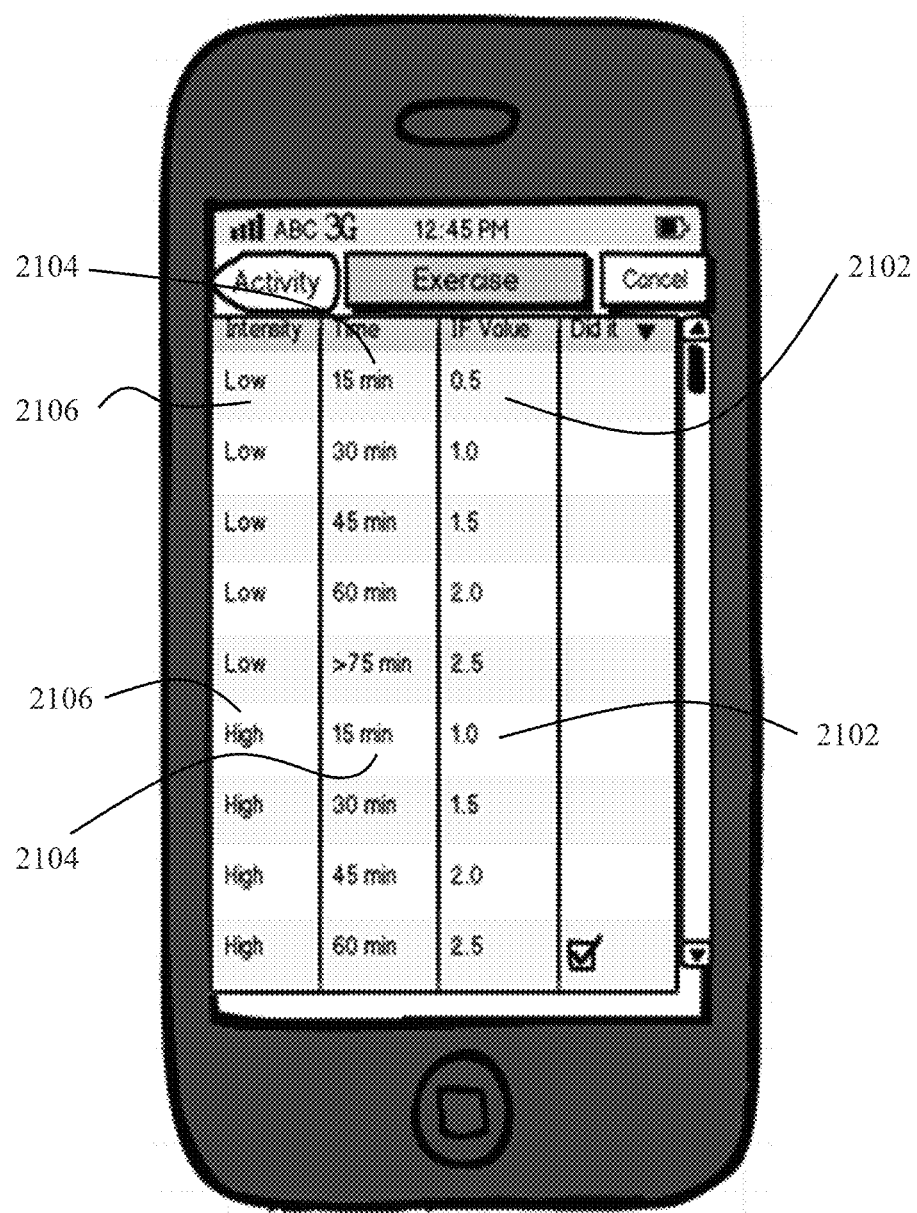
FIG. 21 is an elevational view of the front face of a mobile device featuring a graphical user interface displaying a particular activity item from FIG. 20 for IF Value determination in accordance with the principles of the present invention.

FIGS. 19-21 are elevational views of the front face of the mobile device 100 featuring the wellness application 102 that provides a graphical user interface displaying a user selection for determining IF Values of particular activities. The user first selects "DO" 108 from the menu shown in FIG. 3. The user selects IF values 1902 as shown in FIG. 19. The user is then prompted to select particular activities for logging.

Intensity may be depicted as low, medium or high. Alternatively, intensity may be depicted as any numerical value capable of depicting the intensity, such as an intensity value between one (1) and ten (10).

Figure 22:
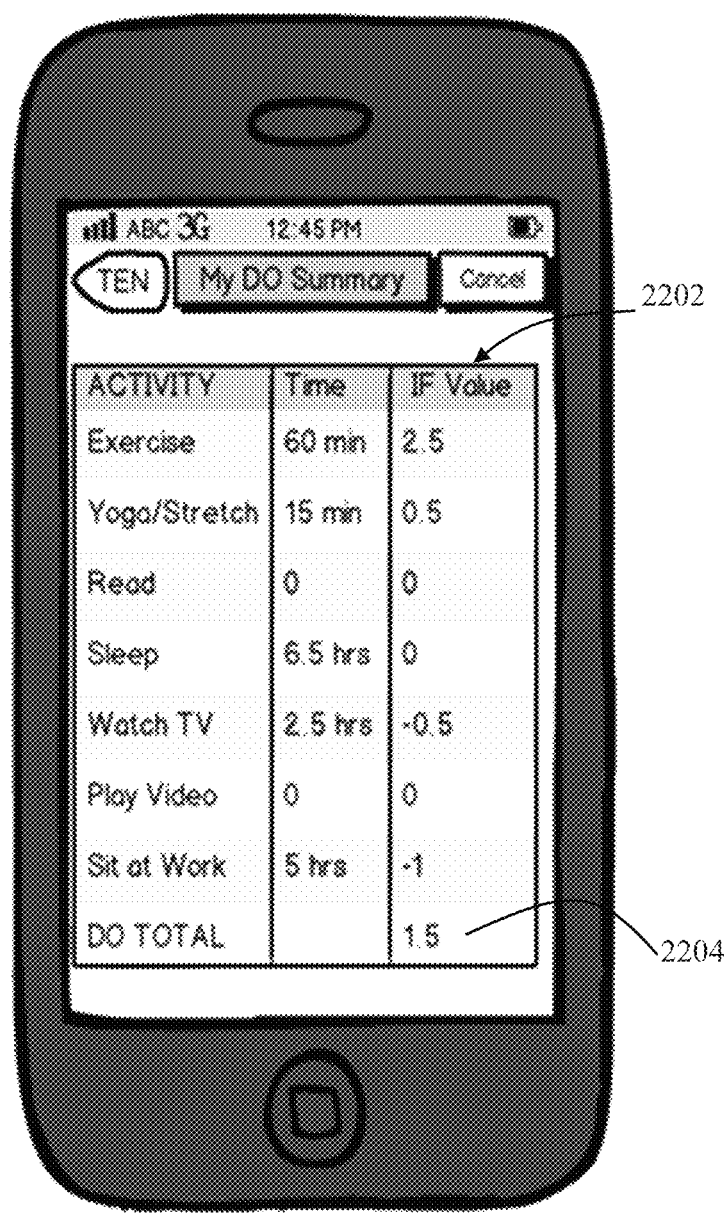
FIG. 22 is an elevational view of the front face of a mobile device featuring a graphical user interface displaying a summary in accordance with the principles of the present invention.
Figure 23:
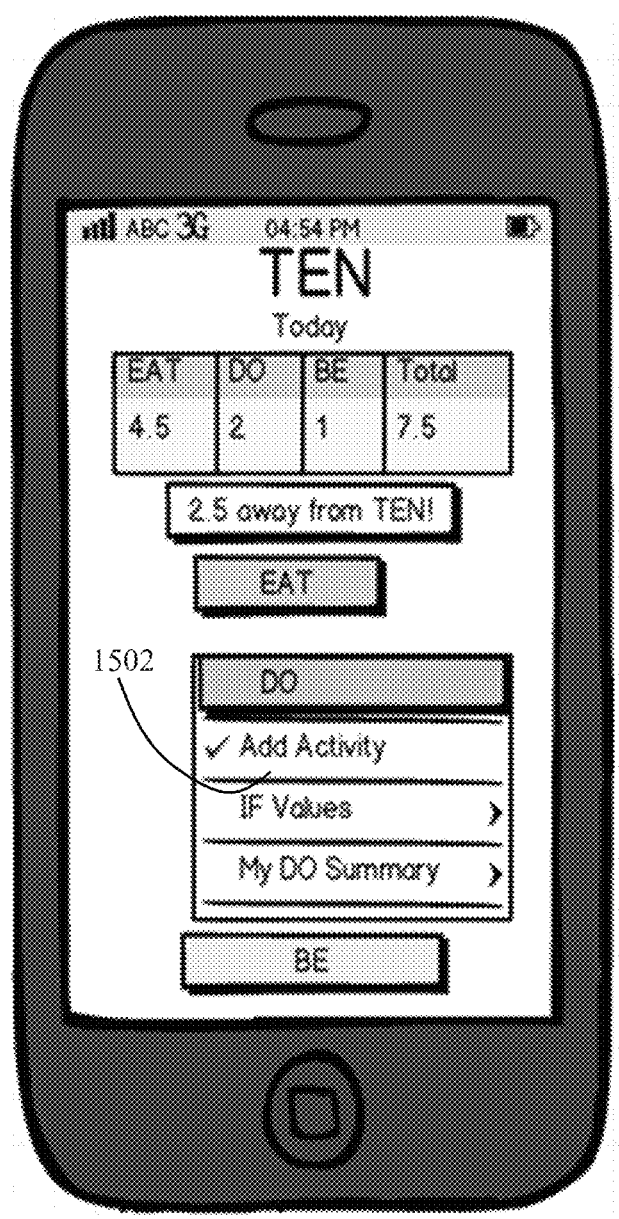
FIGS. 23-26 are elevational views of the front face of a mobile device featuring a graphical user interface displaying selections of an Activity in accordance with the principles of the present invention.
Figure 24:
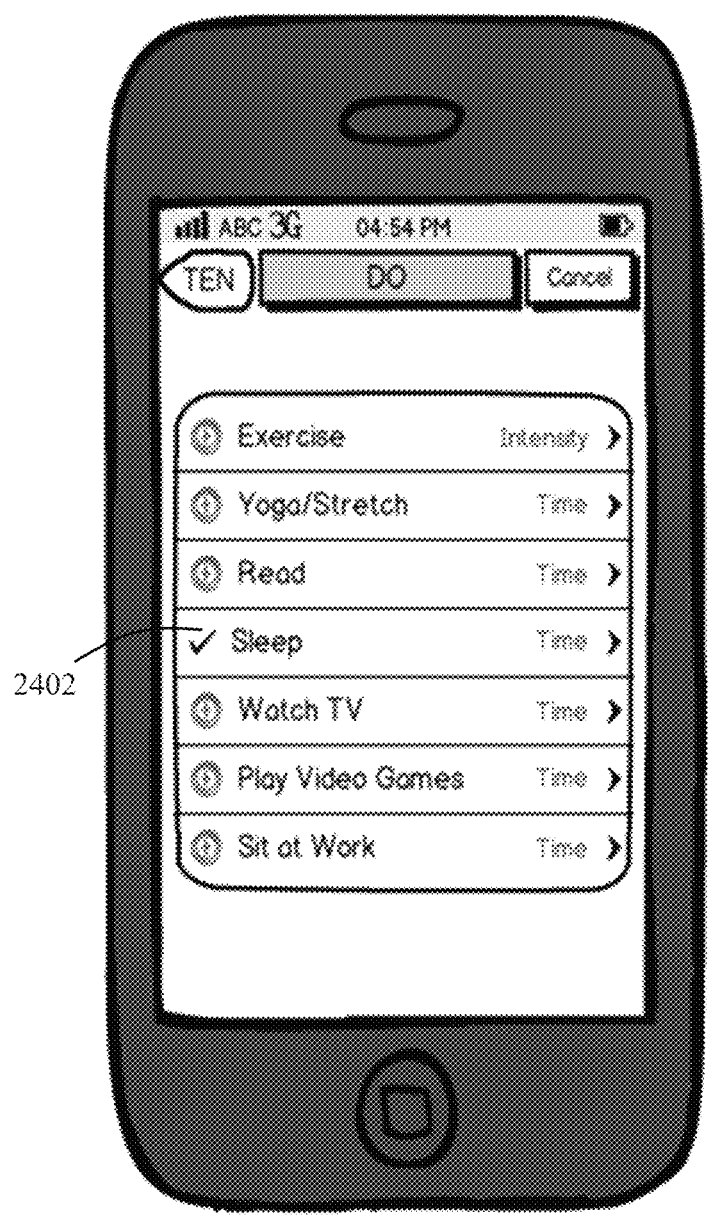

FIG. 22 is an elevational view of the front face of the mobile device 100 featuring the wellness application 102 that provides a graphical user interface displaying a summary 2202 of activities performed by the user. The particular activities are shown along with the duration of the activity and the IF Value associated with the activity. The credits assigned to each activity can be dynamically calculated based on the activity and the time the activity is performed. For instance, a particular credit value, e.g., one (1) can be assigned for running a mile. Only a credit value of half (0.5) is associated with running two (2) miles and a quarter (0.25) for a third mile. This is based on a diminishing returns calculation. A diminishing returns calculation is a method of assigning differing values to the same item based on one or more factors. For example, eating one or two apples has a positive wellness impact and is good; eating 15 apples in one sitting may have a negative wellness impact and is not good. Therefore, the first apple would score a higher credit than would the fourth. As another example, if a user runs one (1) mile, the wellness impact may be greater than would be the last mile of a five-mile run. Therefore, the first mile would score a higher credit value than the fifth. Additionally, frequency of the exercise can impact the credits assigned, e.g., more credit for a first exercise in a long time than for one exercise in a regular and frequent workout routine.

Looking at FIG. 22, a summary 2202 may include the total credit value 2204 associated with the activities performed by the user. The total credit value 2204 is the summation of the total credit value earned for the plurality of activities. Additionally, the item credit value will be subtracted from the target goal 114 (FIG. 1).

Figure 25:
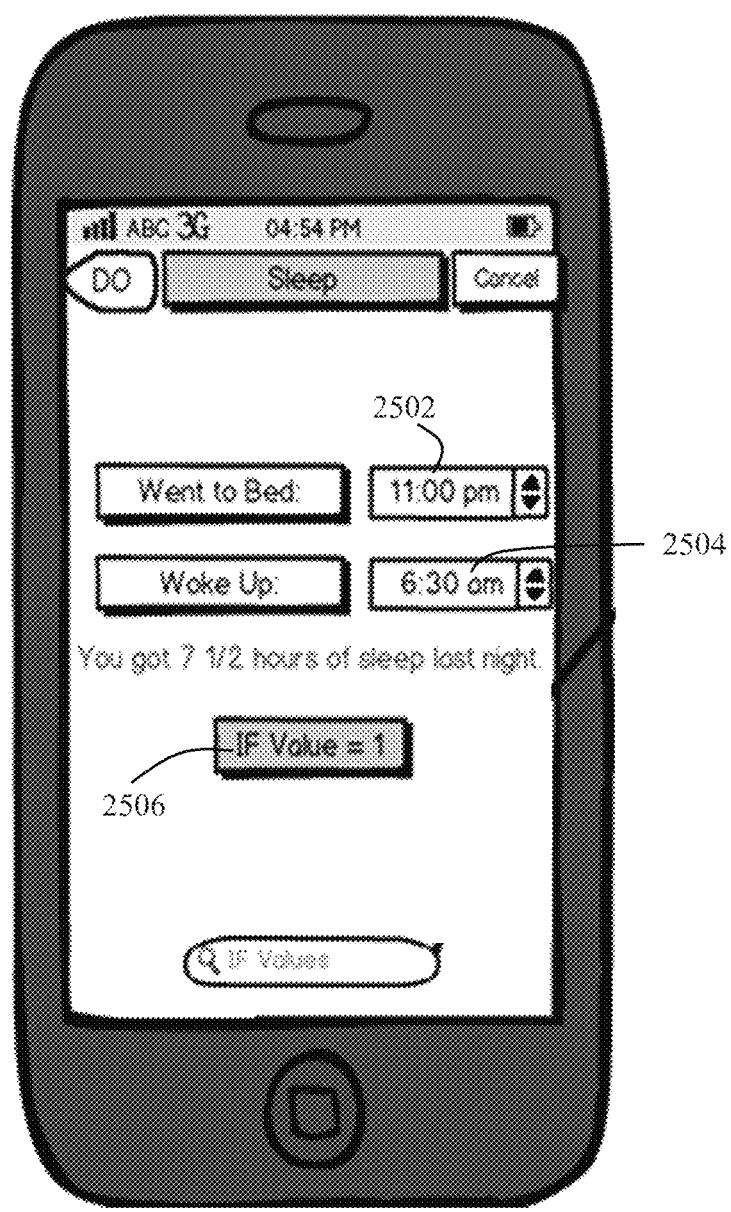
Figure 26:
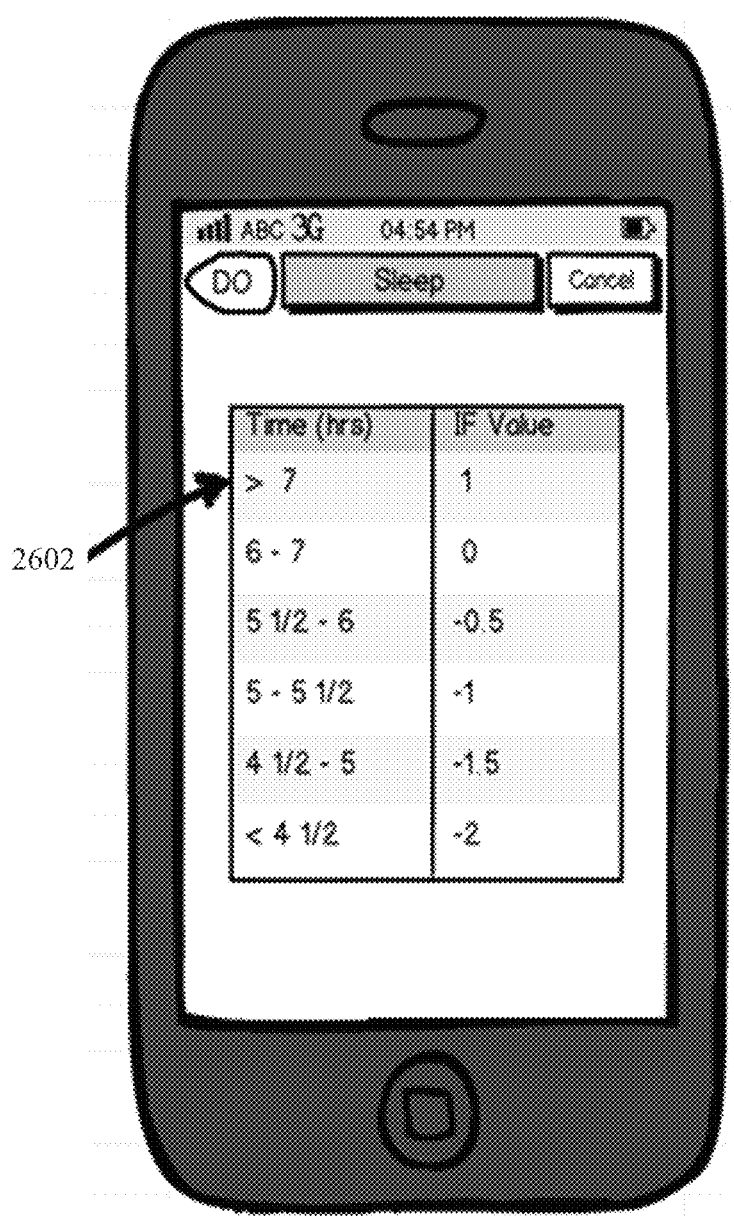

FIGS. 23-26 are elevational views of the front face of the mobile device 100 featuring the wellness application 102 that provides a graphical user interface displaying a user selection for adding credit values associated with particular activities. The user selects "DO" 108, as shown in FIG. 3. Next, the user selects "Add Activity" 1502 from the menu shown in FIG. 23. The wellness application 102 then prompts the user to add particular activities. For example, the user may select "Sleep" 2402 from the menu of FIG. 24. Because both the duration and the timing of sleep is important towards overall health and wellness, selection of sleep 2402 provides for the selection of the time that the user went to bed 2502, as well as the time that the user woke up 2504 (FIG. 25). A credit value is associated with the total duration of the sleep 2504. The user may input the duration of the sleep. Alternatively, the wellness application 102 causes the calculation of the duration of the sleep as relating to the time that the user went to bed 2502 and the time that the user woke up 2504. An IF Value 2506 is associated with the duration of the sleep chosen by the user, exemplified by element 2602 in FIG. 26. Further, the IF Value 2506 may be calculated in relation to the quality of the sleep. For example, the IF Value may increase by any value, such as zero point five (0.5) credits, for good quality sleep. As another example, the IF Value decreases by any value, such as zero point five (0.5), for a poor quality sleep. Further, the credits can exponentially increase or decrease based on the differential between the ideal sleep time and the user. For example, maximum credits can be assigned if the user sleeps 8 hours. Additional credit may be assigned for sleeping more than 8 hours, but the additional credit will not scale. For example, if the credit for sleeping eight (8) hours is two (2) credits, the score for sleeping nine (9) hours will not equal 2.25, i.e., will not be equal to the 8 hour credit divided by 8. This again, follows the theory of diminishing returns.

It should be understood that while the wellness application references particular food items or groups, user selections may be replaced with pictures, icons or other colors codes to communicate information to the user without departing from the spirit of the invention.

While the wellness application 102 is configured to track the IF Values, the user may manually track on paper the total credits earned 104 from the Impact Score without departing from the spirit and scope of the invention. Furthermore, the user may manually calculate the Impact Score using tradition methods of calculation such as a calculator, slider rule or in the user's head. Subsequently, the user will record the IF Value to paper or a journal or other known means for recording information for a particular credit value. Yet further, a booklet having IF Values be provided to the user. The user may manually calculate IF Values based on information in the booklet. For example, the booklet may describe the amount of credits earned or lost for a particular food item, activity or behavior, in accordance with the spirit of the present invention.

In an embodiment, the wellness application 102 is configured to encourage healthy behaviors and actions through feedback of impact of both healthy and unhealthy (1) foods, (2) activities, and (3) behaviors. The wellness application 102 determines a baseline that is used to encourage healthy behaviors. For example, an initial questionnaire may be provided to a user to calculate the baseline. An exemplary questionnaire may request input relating to:

a. Age
b. Height
c. Weight
d. Do you currently smoke?
e. Do you currently eat seafood/fish?
  i. If yes, how many times per week?
  ii. If no, would you eat seafood/fish?
f. On average, how many hours of sleep do you get per night?
g. On average, how many hours of TV do you watch per day?
h. How many hours per day do you sit at work?
i. Do you eat breakfast every morning?
j. Do you eat a piece of fruit every day?
k. Do you eat a vegetable every day?
l. What is the average number of alcoholic drinks that you consume per week?
m. How often do you eat dinner at a restaurant per week?
n. How often do you eat take-out food each week?
o. Do you drink soda?
  i. If yes, how many per week?
p. How much exercise do you perform each week?
q. Do you walk at least 15 minutes every day?

From a questionnaire, the wellness application 102 will show progress and improvement immediately upon beginning the wellness program because the initial information received from the questionnaire will act as a baseline. The progress and improvement may be depicted as a bar graph or some other type of chart. Based on the questionnaire responses, the wellness application 102 suggests foods, activities and behaviors that will allow the user to reach their stated goals. The suggestions may come in the form of alerts to indicate, encourage or otherwise remind the user to reach their goal. Alerts may be text messages, pop-up messages, sound alerts, or any other type of alert capable of alerting or encouraging a user.

In an embodiment, alerts may be generated by the wellness application 102 to encourage and help the user to reach any particular goal stated herein. In an example, the alerts may be based on foods previously consumed and logged. The wellness program 102 will alert the user suggesting the consumption of a particular food item that will help the user reach a particular goal. Alternatively, the alerts may be based on past activities performed and/or past behaviors. In an example, the alerts are based on prior known activities and/or behaviors of the user that evidence a statistically higher likelihood that the user will perform that activity or behavior and thus allow the user to reach a particular goal.

What is claimed is:

1. A process for improving human wellness, the process comprising the steps of:
   receiving at a processing device at least one input based on at least one of a user consumed food, a user activity, and a user behavior;
   assigning a value to each of said at least one input, each value being one of a positive, a negative and a neutral value and derived by a diminishing return calculation, where the value assigned to an $n^{th}$ occurrence of the at least one input that has a sign different from sign of the value assigned to a first occurrence of the at least one input, the $n^{th}$ occurrence is subsequent to the first occurrence, and the value assigned to the $n^{th}$ occurrence is dependent on the value assigned to the first occurrence;
   calculating, based on each value, a total credit value; and
   causing the processing device to display a value related to the total credit value.

2. The method of claim 1 wherein the negative value reduces the total credit value in relation to a target goal.

3. The method of claim 1 wherein the positive value increases the total credit value in relation to a target goal.

4. The method of claim 1 wherein the value is assigned based on a measurement of an amount of the user consumed food.

5. The method of claim 1 wherein the value is assigned based on a nutritional quality of the user consumed food.

6. The method of claim 1 wherein the value is assigned based on a characteristic of other food consumed by the user.

7. The method of claim 1 wherein the value is assigned based on a time of day the user consumed food is consumed.

8. The method of claim 1 wherein the value is assigned based on at least one of a location where the user consumed food is purchased and a location where the user consumed food is consumed.

9. The method of claim 1 wherein the value is assigned based on duration of the user activity.

10. The method of claim 1 wherein the value is assigned based on an intensity level of the user activity.

11. The method of claim 1 wherein the value is assigned based on an intensity level of the behavior.

12. The method of claim 1 wherein the value is assigned based on a duration associated with the behavior.

13. The method of claim 1 wherein the diminishing return calculation assigns less value for a second occurrence of at least one of the user consumed food, the user activity, and the user behavior than for a first occurrence of the user consumed food, the user activity, and the user behavior.

14. A method for tracking health and wellness of a person, the method comprising the steps of:
   receiving at a processing device a plurality of inputs based on a combination of at least one user consumed food, at least one user activity, and at least one user behavior;
   relating at least one positive value to one of the plurality of inputs;
   relating at least one negative value to one of the plurality of inputs;
   calculating a total credit value based on the positive and negative values, the total credit value reduced in relation to the at least one negative value; and
   causing the processing device to display a value related to the total credit value.

15. The method of claim 14 wherein one of the at least one positive value and the at least one negative value is assigned based on at least one of:
   a measurement of an amount of the user consumed food;
   a nutritional quality of the user consumed food;
   a time of day the user consumed food is consumed;
   a location where the user consumed food is consumed; and
   a location where the user consumed food is purchased.

16. The method of claim 14 wherein one of the at least one positive value and the at least one negative value is assigned based on at least one of:
   a duration of the user activity; and
   an intensity level of the user activity.

17. The method of claim 14 wherein one of the at least one positive value and the at least one negative value is assigned based on an intensity level of the behavior.

18. The method of claim 14 wherein one of the at least one positive value and the at least one negative value is assigned based on the duration of the behavior.

19. The method of claim 14 wherein the assigned values are weighted less for a second occurrence of at least one of the user consumed food, the user activity, and the user behavior than for a first occurrence of the user consumed food, the user activity, and the user behavior.

20. A method for improving human wellness, the method comprising the steps of:
   providing a processing device operable to display a user-selectable menu that includes at least two of:
      a user consumed food selection;
      a user activity selection; and
      a user behavior selection;
   receiving at the user-selectable menu at least one input indicating an attribute of at least one of:
      a user consumed food;
      a user activity; and
      a user behavior;
   assigning a value to the at least one input, the assigned value being one of a positive, a negative, and a neutral value and derived by a diminishing return calculation, where the value assigned to an $n^{th}$ occurrence of the at least one input that has a sign different from sign of the value assigned to a first occurrence of the at least one input, the $n^{th}$ occurrence is subsequent to the first occurrence, and the value assigned to the $n^{th}$ occurrence is dependent on the value assigned to the first occurrence;
   calculating, based on each assigned value, a total credit value; and
   causing the processing device to display a value related to the total credit value.

* * * * *